(12) United States Patent
Sardi et al.

(10) Patent No.: US 10,443,062 B2
(45) Date of Patent: Oct. 15, 2019

(54) GENES THAT IMPROVE TOLERANCE TO LIGNOCELLULOSIC TOXINS WHEN OVEREXPRESSED IN YEAST

(71) Applicant: Wisconsin Alumni Research Foundation, Madison, WI (US)

(72) Inventors: Maria Sardi, Madison, WI (US); Audrey P. Gasch, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 15/693,710

(22) Filed: Sep. 1, 2017

(65) Prior Publication Data
US 2018/0073033 A1 Mar. 15, 2018

Related U.S. Application Data

(60) Provisional application No. 62/382,535, filed on Sep. 1, 2016.

(51) Int. Cl.
| | | |
|---|---|---|
| C12N 15/81 | (2006.01) | |
| C12N 9/12 | (2006.01) | |
| C07K 14/395 | (2006.01) | |
| C12N 9/04 | (2006.01) | |
| C12P 7/10 | (2006.01) | |
| C12P 7/64 | (2006.01) | |
| C12N 15/52 | (2006.01) | |

(52) U.S. Cl.
CPC ............ *C12N 15/81* (2013.01); *C07K 14/395* (2013.01); *C12N 9/0006* (2013.01); *C12N 9/1205* (2013.01); *C12N 15/52* (2013.01); *C12P 7/10* (2013.01); *C12P 7/649* (2013.01); *C12Y 101/0117* (2013.01); *C12Y 207/01025* (2013.01); *Y02E 50/13* (2013.01); *Y02E 50/16* (2013.01); *Y02E 50/343* (2013.01)

(58) Field of Classification Search
None
See application file for complete search history.

(56) References Cited

FOREIGN PATENT DOCUMENTS

WO WO2004079008 * 12/2004

OTHER PUBLICATIONS

Accession ADS33300. Aug. 4, 2011 (Year: 2011).*
Accession AY693026. Apr. 24, 2007 (Year: 2007).*
Accession Z28336. Apr. 18, 2005 (Year: 2005).*
Ge et al. Weishengwu Xuebao (2010), 50(6), 762-767. Abstract. (Year: 2010).*
Dogan et al. Appl Biochem Biotechnol. Sep. 2014;174(1):28-42 (Year: 2014).*
Jensen et al. FEMS Yeast Res. Mar. 2014;14(2):238-48 (Year: 2014).*
Gachotte et al. Proc Natl Acad Sci U S A. Nov. 10, 1998;95(23):13794-9. (Year: 1998).*
Accession Q02196. Jul. 1, 1993 (Year: 1993).*
Chica et al. Curr Opin Biotechnol. Aug. 2005;16(4):378-84. (Year: 2005).*
Singh et al. Curr Protein Pept Sci. 2017, 18, 1-11 (Year: 2017).*

* cited by examiner

*Primary Examiner* — Christian L Fronda
(74) *Attorney, Agent, or Firm* — Boyle Fredrickson S.C.

(57) ABSTRACT

The present invention provides isolated gene sequences useful in increasing lignocellulosic toxin tolerance in yeast. Such engineered yeast are useful in methods of biofuel production, particularly ethanol production. Methods of bioengineering recombinant yeast with increased lignocellulosic toxin tolerance are also provided.

10 Claims, 11 Drawing Sheets
(9 of 11 Drawing Sheet(s) Filed in Color)
Specification includes a Sequence Listing.

GENES THAT IMPROVE TOLERANCE TO LIGNOCELLULOSIC TOXINS WHEN OVEREXPRESSED IN YEAST

CROSS-REFERENCE TO RELATED APPLICATIONS

This application claims the benefit of U.S. provisional application No. 62/382,535, filed Sep. 1, 2016, and hereby incorporated by reference.

STATEMENT AS TO RIGHTS TO INVENTIONS MADE UNDER FEDERALLY SPONSORED RESEARCH AND DEVELOPMENT

This invention was made with government support under DE-FC02-07ER64494 awarded by the US Department of Energy. The government has certain rights in the invention.

FIELD OF THE INVENTION

The present invention relates to the production of biofuel. More particularly, the present invention relates to genes that improve tolerance to lignocellulosic toxins when overexpressed in Saccharomyces cerevisiae.

BACKGROUND OF THE INVENTION

Biomass is made up of complex chemicals, and the processes of freeing sugars from the lignocellulosic complexes creates a variety of molecules that prove to be toxic to micro-organisms used for fermentation. Beyond acute toxicity, the fermentation conditions themselves can prove stressful to the organisms negatively affecting ethanol yield. Some of these hydrolysate toxins include amides, weak acids, and aldehydes that have synergistic interactions with other stresses in hydrolysate, including acetate and high osmolarity.

Lignocellulosic plant material is a sustainable and renewable source of biomass for bioenergy and biochemical production. Plant cellulose and hemicellulose harbor significant concentrations of sugars that can be used to produce desired compounds through microbial fermentation. In recent years, several technologies have been developed to hydrolyze plant biomass in order to release monomeric sugars (1, 2). For most types of chemical pretreatment, the resulting hydrolysate contains high sugar concentrations, and thus high osmolarity, and also toxic compounds such as weak acids, furans, and phenolics that are generated as a byproduct of chemical hydrolysis. These hydrolysate toxins (HTs) are known to inhibit microbial growth and fermentation; however, the mechanisms of stress tolerance remain unclear for many of these compounds (3-5). Because removal of these inhibitors from the hydrolysate is expensive (6), a focus is to utilize inhibitor-tolerant microorganisms to produce biofuels and chemicals from plant biomass in an economically viable way.

One approach to this problem is to generate hydrolysate-tolerant microbes by engineering stress tolerance based on the mechanism of toxin action. Most studies elucidating inhibitory mechanisms have focused on individual toxins applied in isolation and have established the effects of such toxins. For example, weak acids such as acetic, formic, and levulinic acids inhibit cell growth and fermentation by mechanisms known as weak acid uncoupling and intracellular anion accumulation (7). Weak acids protonated at low pH can diffuse across the plasma membrane whereupon they dissociate to decrease cytosolic pH (8) and consequently stimulate plasma membrane ATPases that consume ATP to pump protons out of the cell (9, 10). Furans such as 5-hydroxymethyl furfural (HMF) and furfural are also common inhibitors found in hydrolysate, formed by the degradation of xylose and glucose, respectively (7). Furan derivatives are thought to decrease ethanol production by directly inhibiting alcohol dehydrogenase (ADH), pyruvate dehydrogenase (PDH) and aldehyde dehydrogenase (ALDH) enzymes (11). In addition, furfural causes the accumulation of reactive oxygen species that broadly damage membranes, DNA, proteins, and cellular structures (12). Cells respond by reducing furans to less inhibitory compounds at the expense of NAD(P)+ reduction; thus the combined presence of furfural and HMF limits cell division and biofuel production (13, 14). Among other inhibitors, phenolics are the most diverse and the least well understood. These compounds are formed during lignin breakdown, and thus their concentrations and identities mainly depend on the source of plant biomass (4, 15). Phenolic compounds exert considerable inhibitory effects by causing the loss of membrane integrity (16, 17), decreasing cellular ATP (18, 19), causing oxidative damage (17), inhibiting de novo nucleotide biosynthesis (20) and inhibiting translation (21). While the effects of individual toxins are becoming clear in some cases, the compounded effects of multiple toxins in hydrolysate are poorly understood (22, 23). Compounded stress is especially important to consider, since microbes encounter multiple inhibitors at the same time during industrial fermentation of lignocellulosic hydrolysates.

In view of the current state of the biofuel industry, particularly ethanol production based on lignocellulosic feedstocks, it can be appreciated that identifying genes related to enhanced biofuel production is a substantial challenge in the field. Accordingly, a need exists in the field to identify additional genes that influence biofuel production in yeast, and consequently engineer recombinant strains of yeast capable of increased biofuel yields from commonly-available feedstocks, including lignocellulosic plant material.

SUMMARY OF THE INVENTION

The present invention is largely related to the inventors' research efforts to better understand tolerance to lignocellulosic toxins by yeast in the context of biofuel production. With this goal in mind, the inventors utilized high throughput competitive library screening to identify genes involved in lignocellulosic toxin tolerance. This approach implicated a variety of apparently novel genes and processes in toxin tolerance. Several of these genes significantly improved lignocellulosic toxin tolerance when engineered in S. cerevisiae.

Based on the inventors' substantial efforts, the present invention provides, in a first aspect, a recombinant vector comprising: (a) the nucleotide sequence of SEQ ID NO:1, SEQ ID NO:2, or SEQ ID NO:3; or (b) a nucleotide sequence which hybridizes under stringent conditions to SEQ ID NO:1, SEQ ID NO:2, or SEQ ID NO:3 or to a fully complementary nucleotide sequence thereof; and (c) a promoter operably-linked to the nucleotide sequence of (a) or (b); wherein overexpression in yeast of said nucleotide sequence provides increased tolerance to lignocellulosic toxins relative to a control yeast lacking overexpression of the nucleotide sequence.

In certain embodiments, the vector includes heterologous nucleotide sequences that stably maintain the vector at a high copy number when transformed into yeast.

In alternate embodiments, the promoter is a heterologous promoter, as opposed to a native promoter.

In another aspect, the invention encompasses a recombinant yeast comprising a recombinant vector as described and claimed herein.

The recombinant yeast is preferably of the genus *Saccharomyces*, more preferably *Saccharomyces cerevisiae*.

In some embodiments, the recombinant vector is an extrachromosomal vector stably maintained in the recombinant yeast. In alternative embodiments, the recombinant vector is integrated into a chromosome of the recombinant yeast.

In yet another aspect, the invention is directed to a method for producing biofuel by fermentation of a lignocellulosic plant material in yeast, comprising: (a) culturing under biofuel-producing conditions a recombinant yeast according to the invention; and (b) isolating biofuel produced by said recombinant yeast.

The invention further provides a method for producing biofuel by fermentation of a lignocellulosic plant material in yeast, comprising: (a) culturing under biofuel-producing conditions a recombinant yeast transformed with a recombinant nucleic acid that overexpresses an adenylylsulfate kinase (MET14), protein folding protein folding co-chaperone (MDJ1), or C3 sterol dehydrogenase (ERG26); and (b) isolating biofuel produced by said recombinant yeast. The recombinant yeast is preferably *Saccharomyces cerevisiae*.

In certain embodiments, the recombinant nucleic acid is contained in a recombinant vector that is maintained at a high copy number in the recombinant yeast.

Methods of use according to the present invention preferably utilize lignocellulosic plant material that is an ammonia fiber explosion (AFEX)-treated lignocellulosic plant material.

Yet another aspect of the invention provides a recombinant *Saccharomyces cerevisiae* strain, comprising: (a) an isolated nucleotide sequence encoding and overexpressing an adenylylsulfate kinase (MET14), protein folding protein folding co-chaperone (MDJ1), or C3 sterol dehydrogenase (ERG26); (b) or a nucleotide sequence which hybridizes under stringent conditions to said isolated nucleic acid, or to a fully complementary nucleotide sequence thereof; wherein the isolated nucleotide sequence is contained in an extrachromosomal vector maintained at a high copy number in the strain, and said strain exhibits increased tolerance to lignocellulosic toxins relative to a control strain lacking the isolated nucleotide sequence.

As can be appreciated, the present invention contemplates the use of recombinant yeast as described and claimed herein in the production of biofuel, including certain exemplary recombinant *S. cerevisiae* strains specifically identified in this disclosure.

This invention provides the advantage over prior biofuel-producing technologies in that embodiments of the invention utilize or are based on a robust recombinant DNA approach that provides yeast strains with appreciably increased tolerance to lignocellulosic toxins. Other objects, features and advantages of the present invention will become apparent after review of the specification, claims and drawings. The detailed description and examples enhance the understanding of the invention, but are not intended to limit the scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

I. IN GENERAL

Figure 1:
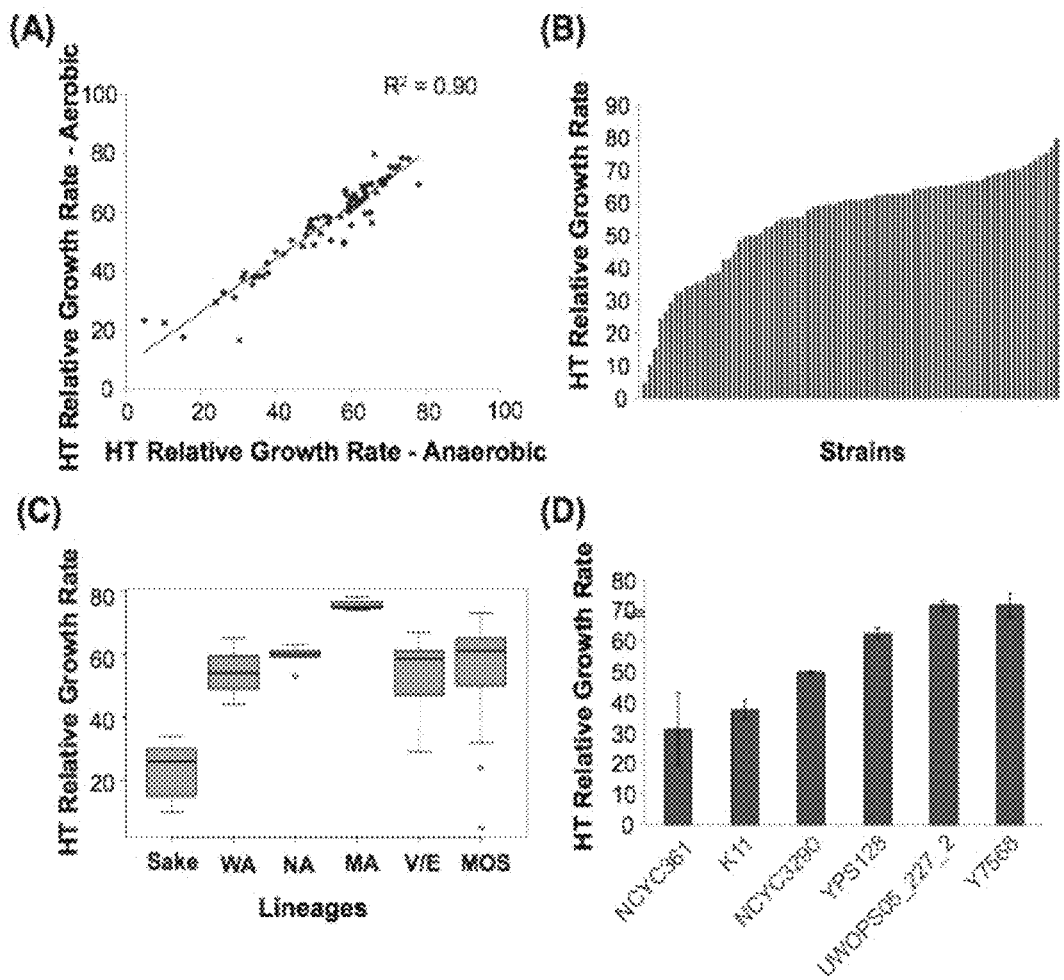
FIG. 1 illustrates strain-specific differences in HT tolerance. HT resistance scores were calculated as outlined in Materials and Methods for 79 strains. (A) HT scores measured in aerobic and anaerobic conditions are highly correlated. (B) The distribution of aerobic HT scores across all strains, where each score represents the average of two biological duplicates for each strain. (C) The distribution of HT scores for each of six lineages: sake, West African (WA), North American (NA), Malaysian (MA), Vineyard/European (V/E), and Mosaic (MOS). (D) The average and standard deviation of HT resistance scores for each of six strains chosen for further analysis.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most cell types at most times are commonly referred to as "constitutive promoters". Promoters that allow the selective expression of a gene in most cell types are referred to as "inducible promoters".

A "host cell" is a cell which has been transformed or transfected, or is capable of transformation or transfection by an exogenous polynucleotide sequence. A host cell that has been transformed or transfected may be more specifically referred to as a "recombinant host cell". Preferred host cells for use in methods of the invention include yeast cells, particularly yeast cells of the genus *Saccharomyces*, more preferably of the species *Saccharomyces cerevisiae*.

The nucleic acid sequence encoding MET14 is recited in SEQ ID NO: 1. The nucleic acid sequence encoding the MDJ1 protein is recited in SEQ ID NO: 2. The nucleic acid sequence encoding the ERG26 protein is recited in SEQ ID NO: 3. SEQ ID NOS:4-6 recite nucleic acids encoding the respective proteins plus native upstream promoter and downstream terminator sequences. SEQ ID NOS:1-6 accompany this specification in Appendix A, which is incorporated by reference in its entirety.

A polypeptide "substantially identical" to a comparative polypeptide varies from the comparative polypeptide, but has at least 80%, preferably at least 85%, more preferably at least 90%, and yet more preferably at least 95% sequence identity at the amino acid level over the complete amino acid sequence, and, in addition, it possesses the ability to increase lignocellulosic toxin tolerance capabilities of a host yeast cell in which is has been engineered and overexpressed.

The term "substantial sequence homology" refers to DNA or RNA sequences that have de minimus sequence variations from, and retain substantially the same biological functions as the corresponding sequences to which comparison is made. In the present invention, it is intended that sequences having substantial sequence homology to the nucleic acids of SEQ ID NO:1, 2 or 3 are identified by: (1) their encoded gene product possessing the ability to increase lignocellulosic toxin tolerance of a host yeast cell in which they have been engineered and overexpressed; and (2) their ability to hybridize to the sequence of SEQ ID NO: 1, 2 or 3, respectively, under stringent conditions.

As used herein, "hybridizes under stringent conditions" is intended to describe conditions for hybridization and washing under which nucleotide sequences that are significantly identical or homologous to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A preferred, non-limiting example of stringent hybridization conditions includes hybridization in 4× sodium chlorine/sodium citrate (SSC), at about 65-70° C. (or hybridization in 4×SSC plus 50% formamide at about 42-50° C.) followed by one or more washes in 1×SSC, at about 65-70° C. A preferred, non-limiting example of highly stringent hybridization conditions includes hybridization in 1×SSC, at about 65-70° C. (or hybridization in 4×SSC plus 50% formamide at about 42-50° C.) followed by one or more washes in 0.3×SSC, at about 65-70° C. A preferred, non-limiting example of highly stringent hybridization conditions includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present invention. SSPE (1×SSPE is 0.15 M NaCl, 10 mM $NaH_2PO_4$, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$[Na+])+ 0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional preferred, non-limiting example of stringent hybridization conditions is hybridization in 0.25-0.5M $NaH_2PO_4$, 7% SDS at about 65° C., followed by one or more washed at 0.02M $NaH_2PO_4$, 1% SDS at 65° C., see e.g., Church and Gilbert (1984) Proc. Natl. Acad. Sci. USA 81: 1991-1995, (or alternatively 0.2×SSC, 1% SDS).

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

The term "isolated nucleic acid" used in the specification and claims means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene. Specifically excluded from this definition are nucleic acids present in mixtures of clones, e.g., as those occurring in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine, as described in a preceding definition.

The term "operably linked" means that the linkage (e.g., DNA segment) between the DNA segments so linked is such that the described effect of one of the linked segments on the other is capable of occurring. "Linked" shall refer to physically adjoined segments and, more broadly, to segments which are spatially contained relative to each other such that the described effect is capable of occurring (e.g., DNA segments may be present on two separate plasmids but contained within a cell such that the described effect is nonetheless achieved). Effecting operable linkages for the various purposes stated herein is well within the skill of those of ordinary skill in the art, particularly with the teaching of the instant specification.

As used herein the term "gene product" shall refer to the biochemical material, either RNA or protein, resulting from expression of a gene.

The term "heterologous" is used for any combination of DNA sequences that is not normally found intimately associated in nature (e.g., a green fluorescent protein (GFP) reporter gene operably linked to a SV40 promoter). A "heterologous gene" shall refer to a gene not naturally present in a host cell (e.g., a luciferase gene present in a retinoblastoma cell line).

As used herein, the term "homolog" refers to a gene related to a second gene by descent from a common ancestral DNA sequence. The term, homolog, may apply to the relationship between genes separated by the event of speciation (i.e., orthologs) or to the relationship between genes separated by the event of genetic duplication (i.e., paralogs). "Orthologs" are genes in different species that evolved from a common ancestral gene by speciation. Normally, orthologs retain the same function in the course of evolution. Identification of orthologs is important for reliable prediction of gene function in newly sequenced genomes. "Paralogs" are genes related by duplication within a genome. Orthologs retain the same function in the course of evolution, whereas paralogs evolve new functions, even if these are related to the original one.

The term "biofuel" refers to a wide range of fuels which are in some way derived from biomass. The term covers solid biomass, liquid fuels and various biogases. For example, bioethanol is an alcohol made by fermenting the sugar components of plant materials and it is produced largely from sugar and starch crops. Cellulosic biomass, such as trees and grasses, are also used as feedstocks for ethanol production and the present invention finds its primary application in this specific field. Of course, ethanol can be used as a fuel for vehicles in its pure form, but it is usually used as a gasoline additive to increase octane and improve vehicle emissions.

"Yeasts" are eukaryotic micro-organisms classified in the kingdom Fungi. Most reproduce asexually by budding, although a few undergo sexual reproduction by meiosis. Yeasts are unicellular, although some species with yeast forms may become multi-cellular through the formation of a string of connected budding cells known as pseudohyphae, or false hyphae, as seen in most molds. Yeasts do not form a single taxonomic or phylogenetic grouping. The term "yeast" is often taken as a synonym for *Saccharomyces cerevisiae*, but the phylogenetic diversity of yeasts is shown by their placement in separate phyla, principally the Ascomycota and the Basidiomycota. The budding yeasts ("true yeasts") are classified in the order Saccharomycetales.

The nucleotides that occur in the various nucleotide sequences appearing herein have their usual single-letter designations (A, G, T, C or U) used routinely in the art. In the present specification and claims, references to Greek letters may either be written out as alpha, beta, etc. or the corresponding Greek letter symbols (e.g., $\alpha$, $\beta$, etc.) may sometimes be used.

II. THE INVENTION

This invention relates to genes that improve yeast tolerance to lignocellulosic plant hydrolysate toxins when over-expressed in yeast, preferably *Saccharomyces cerevisiae*. The inventors used a high-throughput, competitive library screen of three different yeast strains harboring each of ~4,500 gene overexpression plasmids, to identify yeast genes that improve tolerance to lignocellulosic hydrolysate toxins (HTs). The media is designed to mimic the sugar content and so-called 'lignocellulosic' hydrolysate toxins (HTs) found in AFEX-treated corn stover hydrolysate (ACSH). The toxin cocktail includes amides, weak acids, and aldehydes that have synergistic interactions with other stresses in hydrolysate, including acetate and high osmolarity. The inventors identified 85 genes that improve tolerance in at least one of the three strains growing in synthetic medium with sugar and HT content mimicking ACSH. Twenty-eight genes were identified in the thigh-throughput assay that improved tolerance in all three strains. Six of these genes were validated in a single-plasmid assay: three improved strain fitness (based on end-point cell growth) in two or three of the strains tested. These include MET14 (adenylylsulfate kinase) (SEQ ID NO:1), MDJ1 (protein folding co-chaperone) (SEQ ID NO:2), and ERG26 (C3 sterol dehydrogenase) (SEQ ID NO:3).

Accordingly, the present invention is a set of three genes that impart enhanced tolerance to toxins present in biomass hydrolysate. The inventors have demonstrated this enhanced tolerance in a hydrolysate that mimics the hydrolysate produced through AFEX (ammonia fiber explosion) treatment of corn stover. The inventors identified 85 genes that improved tolerance in at least one of the three strains growing in the synthetic AFEX hydrolysate. Subsequent statistical screening narrowed the genes to twenty-eight genes that improved tolerance in all three strains. These genes were validated in a single-plasmid assay: three improved strain fitness (based on end-point cell growth) in two or three of the strains tested. The three *S. cerevisiae* strains tested included oak-soil isolate YPS128, which is very ligno-toxin tolerant strain, NCYC3290 (from a West African beer fermentation) which has medium ligno-toxin tolerance, and sake-making strain K11 which has very low ligno-toxin tolerance. The three genes tested that showed significantly improved growth in at least two of the strains are MET14 (adenylylsulfate kinase), MDJ1 (protein folding co-chaperone), and ERG26 (C3 sterol dehydrogenase). None of these genes has been previously associated with stress tolerance in yeast. Expression of these genes in industrial yeast strains will improve, among many advantages, the ethanol yield from sugars present in AFEX hydrolysate. Presently, the inventors have used a hydrolysate mimic to select for the genes.

As can be appreciated, a major obstacle to sustainable lignocellulosic biofuel production is microbe inhibition by the combinatorial stresses in pretreated plant hydrolysate. Chemical biomass pretreatment releases a suite of toxins that interact with other stressors, including high osmolarity and temperature, which together can have synergistic effects on cells. Yet the combinatorial effects of such stressors as well as the mechanisms cells used to survive them remain unclear. Here, the inventors explored and then exploited natural variation in stress tolerance, toxin-induced transcriptomic responses, and fitness effects of gene overexpression to identify new genes and processes linked to tolerance of hydrolysate stressors. Using six different *Saccharomyces cerevisiae* strains that together maximized phenotypic and genetic diversity, the inventors first explored transcriptomic differences between resistant and sensitive strains to implicate common and strain-specific responses. This comparative analysis implicated primary cellular targets of hydrolysate toxins, secondary effects of defective defense strategies, and mechanisms of tolerance. By dissecting the responses to individual hydrolysate components, the inventors identified synergistic interactions between osmolarity, pH, hydrolysate toxins, and nutrient composition that further inform on defense strategies. High-copy gene overexpression in three different strains revealed the breadth of background-specific effects of gene-fitness contributions in synthetic hydrolysate. The inventors' approach identified new genes for engineering improved stress tolerance while illuminating the effects of genetic background on molecular mechanisms.

Based on the inventors' substantial efforts, the present invention provides, in a first aspect, a recombinant vector comprising: (a) the nucleotide sequence of SEQ ID NO:1, SEQ ID NO:2, or SEQ ID NO:3; or (b) a nucleotide sequence which hybridizes under stringent conditions to SEQ ID NO:1, SEQ ID NO:2, or SEQ ID NO:3 or to a fully complementary nucleotide sequence thereof; and (c) a promoter operably-linked to the nucleotide sequence of (a) or (b); wherein overexpression in yeast of said nucleotide sequence provides increased tolerance to lignocellulosic toxins relative to a control yeast lacking overexpression of the nucleotide sequence.

The recombinant yeast is preferably of the genus *Saccharomyces*, more preferably of the species *S. cerevisiae*. Such recombinant yeast will have at least one copy of a gene which enhances toxin tolerance, and may have two or more, usually not exceeding about 200, depending upon whether the construct is integrated into the genome, amplified, or is present on an extrachromosomal element having multiple copy numbers. Integration or non-integration may be selected, depending upon the stability required for maintenance of the extrachromosomal element, the stability of the particular extrachromosomal element prepared, the number of copies desired, the level of transcription available depending upon copy number, and the like.

As used herein, the term "high copy number" when referring to a recombinant vector shall refer to a vector maintained at about 50 or more copies per haploid genome of yeast cells.

As can be appreciated, the present invention contemplates the use of recombinant yeast as described herein for use in the production of biofuel, including certain exemplary recombinant *S. cerevisiae* strains specifically identified herein, including, as previously-described, e.g., YPS128, NCYC3290, and K11.

The present invention will, in certain embodiments, employ strong heterologous promoters, preferably inducible versions thereof. Suitable promoters for use in the invention include, e.g., the ACT1, PGK1, TDH3, TEF1, or TEF2 promoters, or promoters of other highly expressed *S. cerevisiae* genes. In some embodiments, the promoter is an inducible heterologous promoter and enhanced toxin tolerance in the recombinant yeast is conferred by induction of the inducible heterologous promoter. Inducible heterologous promoters suitable for use in the present invention include, e.g., the GAL4, CUP1, PHO5, or tetO7 promoter.

The present invention further encompasses a method of providing a recombinant yeast useful in biofuel production. Such a method includes steps of introducing into yeast an isolated nucleic acid having: (a) the nucleotide sequence of SEQ ID NO:1, SEQ ID NO:2, or SEQ ID NO:3; or (b) a nucleotide sequence which hybridizes under stringent conditions to SEQ ID NO:1, SEQ ID NO:2, or SEQ ID NO:3, or to a fully complementary nucleotide sequence thereof, wherein overexpression in the yeast of the isolated nucleic acid provides increased tolerance to a lignocellulosic toxin in the yeast relative to a control yeast lacking overexpression of the isolated nucleic acid.

Nucleic acid constructs useful in the invention may be prepared in conventional ways, by isolating the desired genes from an appropriate host, by synthesizing all or a portion of the genes, or combinations thereof. Similarly, the regulatory signals, the transcriptional and translational initiation and termination regions, may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various nucleic acids and/or fragments thereof may be combined, cloned, isolated and sequenced in accordance with conventional ways. After each manipulation, the DNA fragment or combination of fragments may be inserted into a cloning vector, the vector transformed into a cloning host, e.g., *Escherichia coli*, the cloning host grown up, lysed, the plasmid isolated and the fragment analyzed by restriction analysis, sequencing, combinations thereof, or the like.

Various vectors may be employed during the course of development of the construct and transformation of host cells. The vectors may include cloning vectors, expression vectors, and vectors providing for integration into the host or the use of bare DNA for transformation and integration. The cloning vector will be characterized, for the most part, by having a replication origin functional in the cloning host, a marker for selection of a host containing the cloning vector, may have one or more polylinkers, or additional sequences for insertion, selection, manipulation, ease of sequencing, excision, or the like. In addition, shuttle vectors may be employed, where the vector may have two or more origins of replication, which allows the vector to be replicated in more than one host, e.g., a prokaryotic host and a eukaryotic host.

Expression vectors will usually provide for insertion of a construct which includes the transcriptional and translational initiation region and termination region or the construct may lack one or both of the regulatory regions, which will be provided by the expression vector upon insertion of the sequence encoding the protein product. Thus, the construct may be inserted into a gene having functional transcriptional and translational regions, where the insertion is proximal to the 5'-terminus of the existing gene and the construct comes under the regulatory control of the existing regulatory regions. Normally, it would be desirable for the initiation codon to be 5' of the existing initiation codon, unless a fused product is acceptable, or the initiation codon is out of phase with the existing initiation codon. In other instances, expression vectors exist which have one or more restriction sites between the initiation and termination regulatory regions, so that the structural gene may be inserted at the restriction site(s) and be under the regulatory control of these regions. Of particular interest for the subject invention as the vector for expression, either for extrachromosomal stable maintenance or integration, are constructs and vectors, which in their stable form in the host are free of prokaryotic DNA.

For extrachromosomal stable maintenance, it may be necessary to provide for selective pressure on those hosts maintaining the construct. Stable maintenance may be achieved by providing for resistance against a cytotoxic agent, e.g., an antibiotic, such as kanamycin or G418, or by imparting prototrophy to an auxotrophic host. For stable maintenance in a yeast host, the 2 micron origin of replication may be employed or a combination of a centromere, e.g., CEN3, and ars. For integration, generally homologous integration will be desirable, so that the construct will be flanked by at least about 50 bp, more usually at least about 100 bp on each side of the construct of a sequence homologous with a sequence present in the genome of the host.

The yeast host may be transformed in accordance with conventional ways. Conveniently, yeast protoplasts may be transformed in the presence of a fusogen, such as a non-ionic detergent, e.g., polyethyleneglycol.

Yeast strains that may serve as yeast hosts include, for example, certain yeast strains useful in biofuel production such as, e.g., BY4741, YB210, CEN.PK, PE-2, BG-1, CAT-1, SA-1, VR-1 or 424A(LNH-ST) and derivatives thereof. In certain yeast strains, particularly *S. cerevisiae*, the strains may be engineered to contain additional genes such as, e.g., the XYL1, XYL2 and XYL3 genes of *P. stipitis*, which are generally required for most *S. cerevisiae* strains to ferment xylose. Of course, alternative genes of roughly equal function may be used in certain embodiments; e.g., xylose isomerase (XI) may substitute for XYL1/2 in alternative embodiments, and yet other yeast strains may be engineered to include XYL1 and XYL2 genes of *P. stipitis* but rely on native *S. cerevisiae* XYL3. Cassettes containing one or more of XYL1, XYL2 and XYL3 are available in the field. For example, XYL nucleotide sequences from *P. stipitis* CB56054 are available at Accession numbers: XYL1: mRNA=XM_001385144, protein=XP-001385181; XYL2: mRNA=XM-001386945, protein=XP-001386982; and XYL3: mRNA=AF127802, protein=AAF72328. Yet other embodiments may contain one or more of the CtAKR, SpNA, and SpXVT1 genes useful in increased xylose fermentation.

In yet another aspect, the invention is directed to a method for producing biofuel by fermentation of a lignocellulosic plant material in yeast, comprising: (a) culturing under biofuel-producing conditions a recombinant yeast according to the invention; and (b) isolating biofuel produced by said recombinant yeast.

The invention further provides a method for producing biofuel by fermentation of a lignocellulosic plant material in yeast, comprising: (a) culturing under biofuel-producing conditions a recombinant yeast transformed with a recombinant nucleic acid that overexpresses an adenylylsulfate kinase (MET14), protein folding co-chaperone (MDJ1), or C3 sterol dehydrogenase (ERG26); and (b) isolating biofuel produced by said recombinant yeast. The recombinant yeast is preferably *Saccharomyces cerevisiae*.

In certain embodiments, the recombinant nucleic acid is contained in a recombinant vector that is maintained at a high copy number in the recombinant yeast.

Methods of use according to the present invention preferably utilize lignocellulosic plant material that is an ammonia fiber explosion (AFEX)-treated lignocellulosic plant material.

Useful recombinant yeast for biofuel production methods are based on *S. cerevisiae*, particularly strains that have been engineered to carry one or more of the genes described and claimed herein. Accordingly, yet another aspect of the invention provides a recombinant *Saccharomyces cerevisiae* strain, comprising: (a) an isolated nucleotide sequence encoding and overexpressing an adenylylsulfate kinase (MET14), protein folding protein folding co-chaperone (MDJ1), or C3 sterol dehydrogenase (ERG26); (b) or a nucleotide sequence which hybridizes under stringent conditions to said isolated nucleic acid, or to a fully complementary nucleotide sequence thereof; wherein the isolated nucleotide sequence is contained in an extrachromosomal vector maintained at a high copy number in the strain, and said strain exhibits increased tolerance to lignocellulosic toxins relative to a control strain lacking the isolated nucleotide sequence.

In view of the various industrial uses and storage conditions the present recombinant yeasts will be subjected to, the invention further encompasses yeast inoculums which contain at least (a) a recombinant yeast engineered to contain and overexpress one or more of the isolated nucleic acids having: (a) the nucleotide sequence of SEQ ID NO:1, SEQ ID NO:2, or SEQ ID NO:3; or (b) a nucleotide sequence which hybridizes under stringent conditions to SEQ ID NO:1, SEQ ID NO:2, or SEQ ID NO:3, or to a fully complementary nucleotide sequence thereof, wherein overexpression in the yeast of the isolated nucleic acid provides increased tolerance to lignocellulosic toxins in the yeast relative to a control yeast lacking overexpression of the isolated nucleic acid; and (b) a culture medium.

The following experimental data are provided to illustrate the invention. It is to be understood that a person skilled in the art who is familiar with the methods may use other yeast strains, recombinant vectors, and methodology which can be equally used for the purpose of the present invention. These alterations are included in the scope of the invention.

III. EXAMPLES

In this section, the inventors describe various materials, methods and results related to and supportive of the present invention.

Example 1. Leveraging Multi-level Natural Variation Across *Saccharomyces cerevisiae* Isolates to Improve Lignocellulosic Hydrolysate Tolerance This example describes a strategy to both identify strains for industrial use and understand toxin effects by comparing and contrasting yeast strains with differential toxin tolerance. Most of the studies trying to elucidate the mechanisms of toxin inhibition have used lab-domesticated strains, which poorly represent the stress-tolerance potential of the species (24-26). By studying wild isolates that display substantial genetic and phenotypic differences, the inventors can identify variation that may provide previously unrecognized modes of protection against toxins. Here, the inventors leveraged natural diversity in distinct lineages of *Saccharomyces cerevisiae* to explore strain-specific responses to a synthetic mimic of ammonia fiber expansion (AFEX)-pretreated corn stover (ACSH) (23, 27). Using a synthetic hydrolysate allowed us to dissect the transcriptional response to the base-media composition, toxin cocktail, pH, and their combination. Comparing strains of different resistances to the hydrolysate provided key insights into toxins' primary targets and the effects on cellular physiology, which implicated active mechanisms to reduce toxins into less inhibitory components as well as repairing cellular damage. Due to the complex response required to survive the combinatory effects of toxins and other stresses found in the hydrolysate, the inventors explored the role of genetic background on toxin tolerance strategies, uncovering strain specific effects. Interestingly, the group of genes that provide fitness benefits to one or more strains growing in synthetic hydrolysate shows low overlap with genes whose expression responds to hydrolysate, indicating that combining methodologies provides a broader view of cellular defense strategies and genetic background effects. Together, the inventors' efforts provide a glimpse into natural variation in toxin tolerance while implicating mechanisms and genes important for hydrolysate tolerance.

Results

Wide range of HT tolerances across *Saccharomyces cerevisiae* strains. The inventors investigated the response of diverse *S. cerevisiae* strains to lignocellulosic hydrolysate, by phenotyping growth rates of 79 strains grown in base medium with and without toxins. The strains collection included isolates from a variety of niches and geographical locations and encompassed representatives of five of the defined genetic lineages in *S. cerevisiae* (i.e. Malaysian, West African, North America, vineyard/European, and sake/Asian strains) (Liti et al. 2009). The group also included strains domesticated to ferment wine, beer, and sake, strains used to produce biofuel, and wild strains isolated from trees and spoiled fruits (Table 1). Strains were grown in a synthetic hydrolysate mimic of ACSH called SynH. A phenotypic score representing resistance to hydrolysate toxins (HTs) was calculated for each strain as the relative growth rate in complete SynH, which contains the full cocktail of HTs, versus in the hydrolysate mimic without the toxin cocktail (SynH –HTs), in both aerobic and anaerobic conditions. Resistance to HTs was highly correlated regardless of oxygen availability ($R^2$=0.9) (FIG. 1A); thus, the inventors focused on aerobic conditions for simplicity.

The inventors found a wide distribution of toxin-resistance phenotypes, suggesting that HT tolerance is a complex trait in yeast (FIG. 1B, Table 1). Interestingly, the differences in phenotype could be partly explained by lineage-specific differences. The inventors grouped strains based on genetic lineages defined by previous population analyses of *S. cerevisiae* (26, 28-30). Strains of the sake/Asian lineage are the most sensitive to HTs, while Malaysian strains display the highest resistance (FIG. 1C). Strains of the vineyard/European lineage, along with mosaic strains that show admixture from different lineages, showed the widest distribution of phenotypes. The lineage-specific effects are consistent with several other studies that showed lineage-associated traits across strains (24-26, 30, 31). To explore phenotypic differences in *S. cerevisiae*, the inventors chose six strains that would maximize the phenotypic and genetic diversity for further analysis. Five of the strains came from clean lineages: fermentation strain NCYC361 of the vineyard/European lineage, sake-producing strain K11, West African strain NCYC3290 isolated from bili wine, North American oak-tree isolate YPS128, and Malaysian strain UWO.SO5.22-7. The inventors also included one mosaic strain Y7568, isolated from a rotten papaya, which had particularly high HT tolerance (FIG. 1D). Both the vineyard/European and sake strains grow slower in rich lab medium than the rest of the strains (~90 min versus ~70 min, doubling time); however, their growth is comparable to well-studied lab strains ((32) and data not shown). The phenotypes of these six strains represented the distribution seen for all strains in the collection: the sake and vineyard strains displayed ~70% decreased growth rate in the presence of HTs, the West African strain displayed medium sensitivity with ~56% decreased growth rate, and the North American, Malaysian, and mosaic strains displayed a less-than 35% decrease in growth rate when exposed to HTs.

Natural Variation in the Transcriptome Response to Lab Media Implicates Strain Specific States.

To explore the diverse transcriptome response among strains coming from different ecological niches, the inventors started by profiling transcriptome differences across the six natural isolates growing in rich, non-stress laboratory medium (YPD), through RNA-sequencing in biological duplicate. The inventors found 4,523 genes whose expression was significantly different (false discovery rate, FDR <1%) in one or more strains compared to the mean of all strains, representing 72% of all genes. Of these genes, 2,214 had at least a 2-fold expression difference in one or more strains compared to the mean expression level for that gene across all six strains.

Hierarchical clustering analysis revealed that many of the differentially expressed genes were specific to the HT-sensitive strain NCYC361, in which 1,200 genes were differentially expressed compared to the mean of all strains. Expression at 858 of these genes was similarly skewed in the HT-sensitive sake strain K11. These genes primarily displayed higher expression in these strains and were enriched for genes involved in detoxification (Bonferroni-corrected P=3.2e−8, hypergeometric test), for targets of the transcription factor Gln3 that responds to nitrogen limitation (P=0.001), and for thiamine genes (P=0.0004). However, unlike any other isolate, NCYC361 showed induction of the environmental stress response (ESR) (33) even in the absence of added stress (P<9.83e−121). The inventors noticed that this strain has higher expression of genes involved in iron homeostasis (P=1.2e−11) but lower expression of genes involved in the electron transport chain, amino acid biosynthesis, and lipid biosynthesis, compared to the mean of all strains (P=4.71e−13, 2.386e−10, 8.963e−10, respectively). This transcriptional response can be a signature of iron starvation (34), suggesting that NCYC361 may have a defect in iron uptake/metabolism in YPD. Indeed, the inventors found that iron supplementation to YPD partially alleviated the slow growth of this strain specifically (FIG. 1).

Because specific effects in this strain obscured the broader dataset, the inventors removed NCYC361 from the analysis and performed differential expression among the remaining strains. The inventors found 3,323 genes with significant expression differences in one or more strains compared to the mean expression of that gene in the remaining strains; 1,036 of these displayed at least 2-fold differences from the mean. Further analysis of genes differentially expressed across strains revealed strain-specific transcript signatures related to thiamine, sterol, and amino acid biosynthesis among others functional responses.

Figure 2:
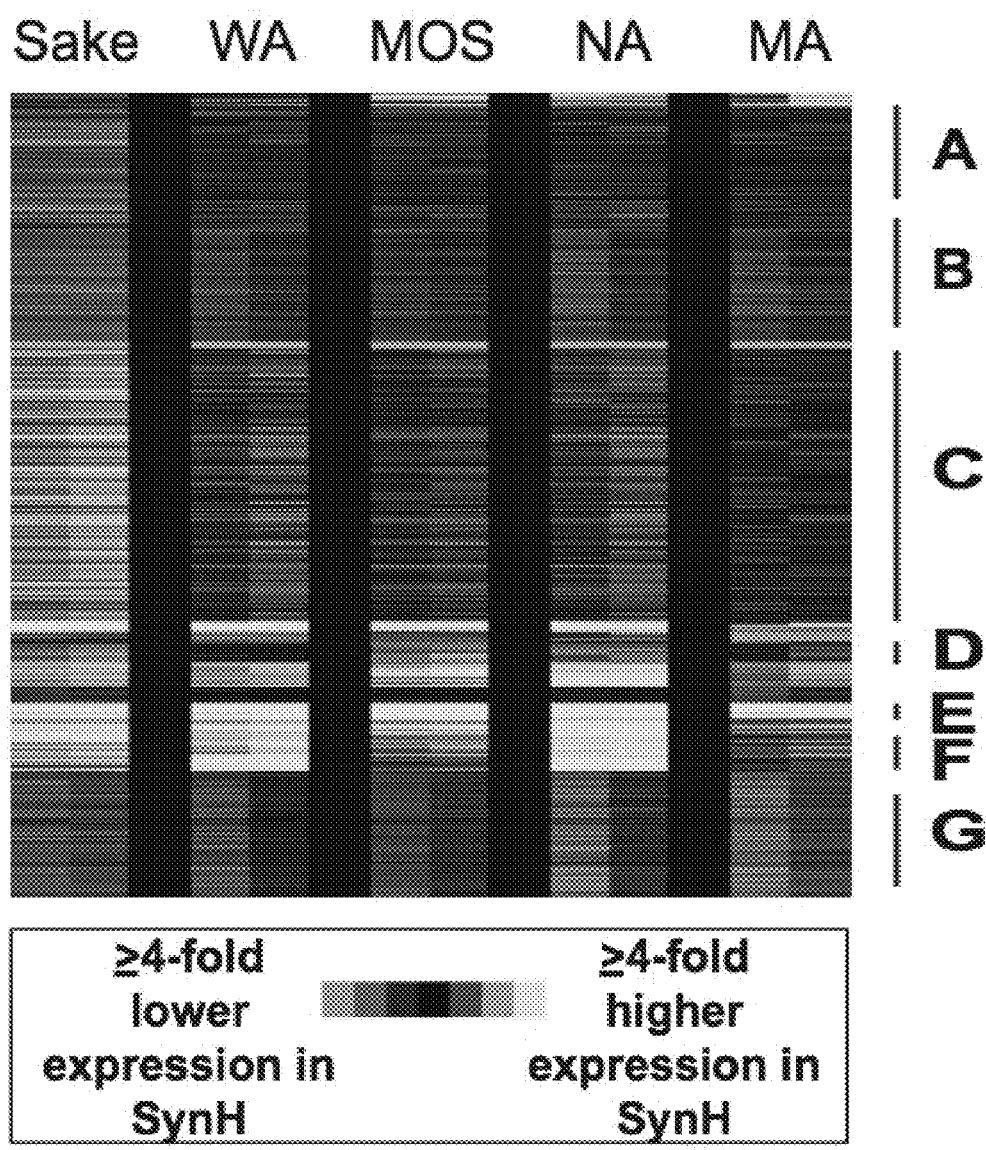
FIG. 2 depicts expression responses to SynH versus rich lab media. Shown are 2,073 differentially expressed genes identified by the linear model, as expressed in strain K11 (Sake), NCYC3290 (WA), Y7568 (MOS), YPS128 (NA), and UWO.SO5.22-7 (MA). Each row represents expression of a given gene and each column represents each of two biological replicates for each strain. Yellow indicates higher expression in the denoted strain growing in SynH versus YPD and blue represents lower expression in SynH compared to YPD, with fold-change according to the key. The data were organized by hierarchical clustering. Functional enrichments were assessed for each cluster, and those that passed a bonferroni corrected p<0.01 included ergosterol biosynthesis (A), protein synthesis genes normally repressed in the ESR (B), aerobic respiration (C), Gcn4 gene targets (D), sulfate assimilation (E), genes normally induced in the ESR along with Sko1 targets (F), and ribosome biogenesis genes normally repressed in the ESR (G).

Transcriptome Responses to SynH with and without HTs Implicates Common and Strain-Specific Toxin Responses To investigate how genetically distinct isolates experience the stress found in lignocellulosic hydrolysate, the inventors investigated strains' transcriptome changes while growing in SynH compared to YPD lab medium. NCYC361 was removed from the analysis due to its aberrant response even in lab medium. A linear model was used to identify genes differentially expressed in each strain, in each media condition, and in a manner affected by a strain-by-media ("Gene by Environment") interaction. The inventors identified 2,073 genes that were differentially expressed in response to SynH compared to YPD (FDR <0.01): 1,884 genes were differentially expressed regardless of the strain, while 740 genes showed a strain-by-media interaction (FIG. 2).

Among the common responses to SynH were activation of the ESR, repression of ergosterol biosynthetic genes (P=0.023), and induction of targets of transcription factor Sko1 that responds to osmotic stress (P=0.01). Expression of genes involved in aerobic respiration (P=7.41e−10) were increased in most strains, most highly in the HT-sensitive strain K11 and least strongly in the most resistance Malaysian strain. The inventors also observed strong induction of genes involved in sulfate assimilation (P=2.46e−7) as well as a broader set of genes regulated by the transcription factor Gcn4, which is activated by amino acid starvation (P=1.18e−6). Higher expression of Gcn4 targets raised the possibility that strains experienced amino acid starvation in SynH compared to rich YPD medium, especially given the stark differences in media composition.

One key advantage of synthetic hydrolysate is that the effects of nutrient availability and HTs can be dissected, by omitting toxins from the recipe. The inventors therefore profiled transcriptional changes provoked by SynH without toxins (SynH −HTs), to distinguish the stress responses specific to the base SynH −HT medium and responses unique to the toxin cocktail. The inventors analyzed the response to SynH −HTs compared to YPD (omitting the wine strain NCYC361 from the analysis) and found 970 genes differentially expressed regardless of the strain and 394 genes with strain-by-media interactions (FDR <0.01).

Figure 3:
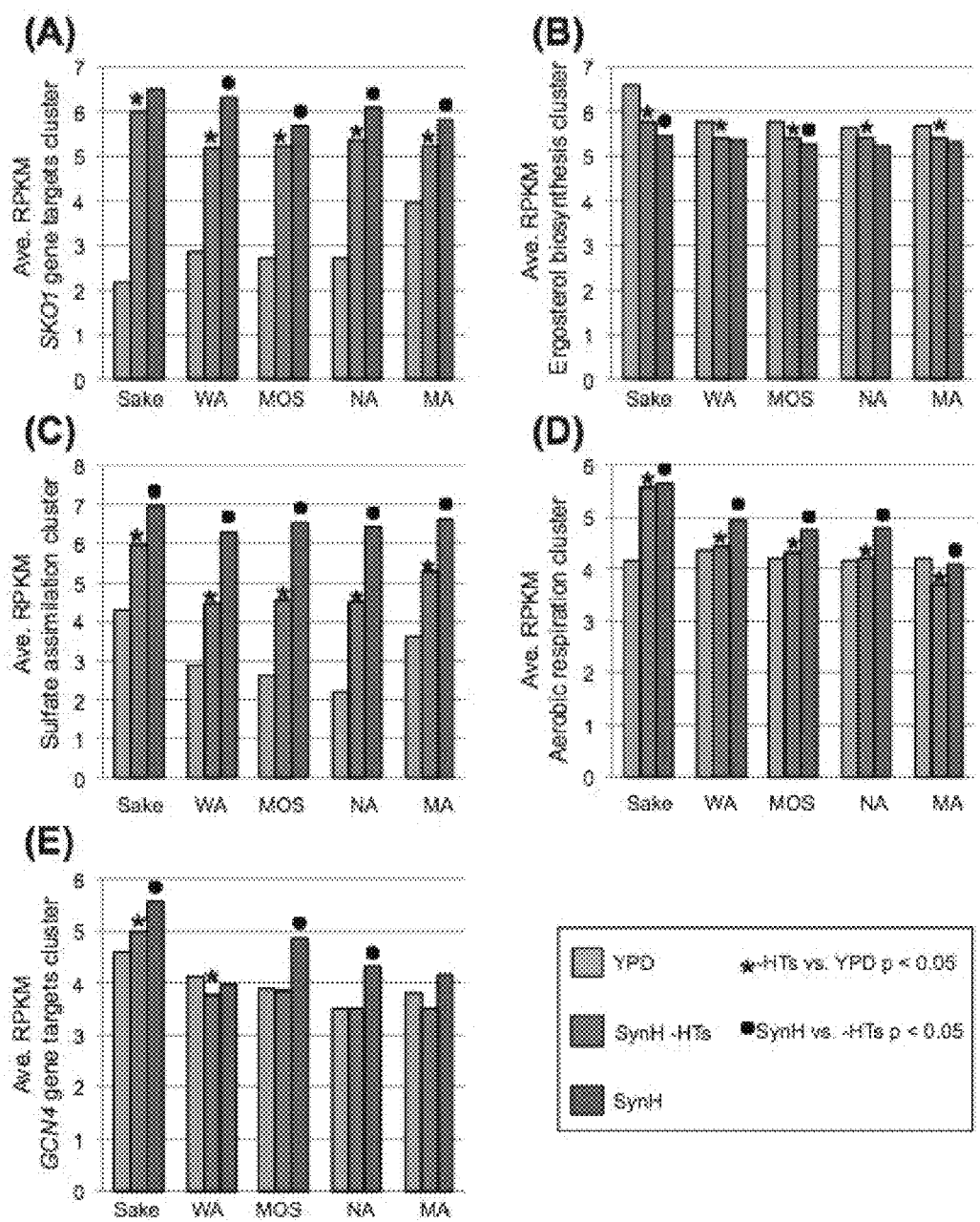
FIG. 3 illustrates expression differences for key groups of genes. Transcriptome differences across strains and media for specific gene clusters. Each histogram represents the average expression level (Log 2 RPKM values, see Methods) of specified genes as measured in two biological replicates for strain K11 (sake), NCYC3290 (WA), Y7568 (MOS), YPS128 (NA), and UWO.SO5.22-7 (MA). Gene clusters were selected based on hierarchical clustering of the various datasets. (A) 27 genes enriched for Sko1 targets, (B) 317 genes enriched for ergosterol biosynthesis genes, (C) 27 genes enriched for sulfate assimilation genes, (D) 236 genes involved in aerobic respiration, (E) 50 genes enriched for targets of Gcn4. An asterisk indicates a significant difference in expression for that gene group in SynH HTs versus YPD, and a circle indicates significant differences in expression in SynH versus SynH –HTs (p<0.05, T-test across all genes in each group).

This analysis distinguished several of responses to SynH that are primarily due to the base medium composition separate from the toxins, and responses common to most or all strains. Genes regulated by the osmo-induced Sko1 transcription factor were induced by SynH −HTs, consistent with the high osmolarity of the base medium (FIG. 3A), while genes involved in ergosterol biosynthesis were repressed in response to SynH −HT medium (FIG. 3B). However, both of these responses were exacerbated in a statistically significant manner in the presence of HTs and in several strains. This pattern was also true for genes linked to sulfate metabolism (FIG. 3C), which were induced by SynH −HTs but expressed even higher in SynH with HTs. Thus, several responses to the base medium were amplified by the presence of toxins, suggesting complex interactions (see Discussion).

Figure 9:
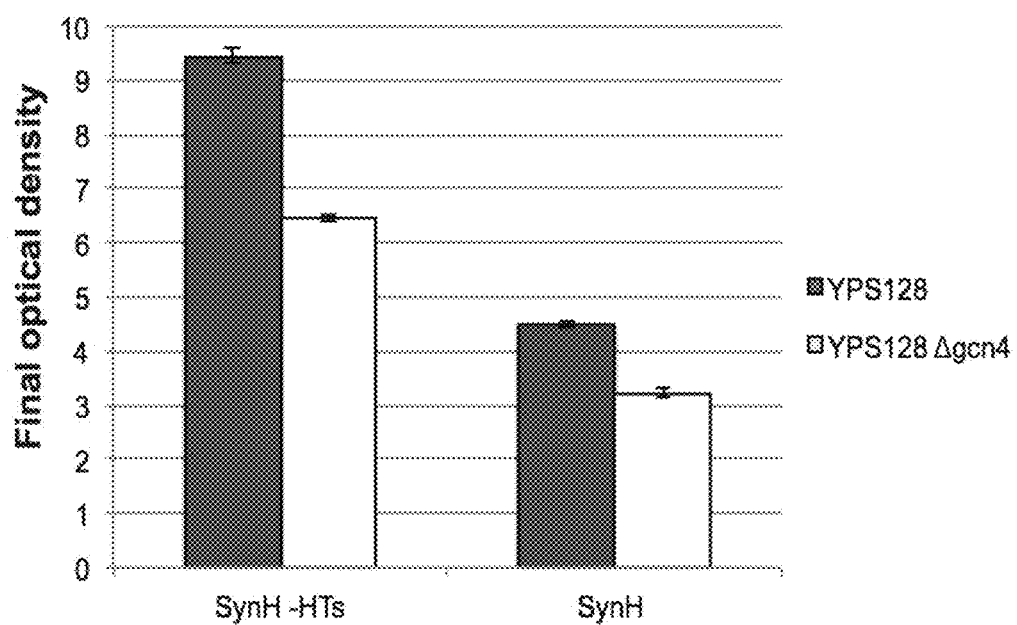
FIG. 9 illustrates how deleting GCN4 reduces growth in both SynH −HTs and SynH. Final cell density after 24 hour growth in each medium was measured for HT-resistant strain YPS128 and YPS128 gcn4D::KanMX. Shown is the average and standard deviation of two biological replicates in SynH −HTs and SynH.

Other responses were specific to the presence of the toxins. For example, genes involved in aerobic respiration were generally expressed more specifically in response to toxins (FIG. 3D). Surprisingly, amino-acid biosynthetic genes regulated by the Gcn4 transcription factor were induced specifically in response to toxins and not in response to the base SynH −HTs medium in most strains (FIG. 3E). Thus induction of amino acid biosynthetic genes is not due to lower amino acid concentrations in SynH but a direct response to the toxins. Addition of amino acids, either as pools or individually, to the SynH medium did not alleviate growth inhibition (data not shown). Deleting GCN4 in HT-resistant strain YPS128 significantly reduced the growth of that strain but in a manner that was not specific to the presence of HTs (FIG. 9). Thus, the HT-dependent induction of Gcn4 targets may reflect an indirect response to toxins, perhaps the accumulation of uncharged tRNAs (35).

Figure 4:
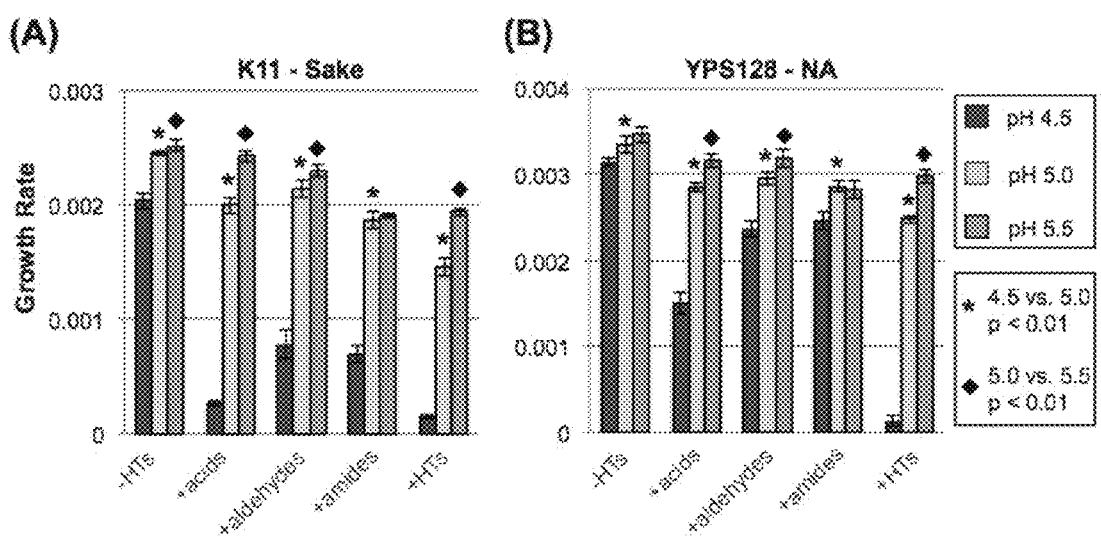
FIG. 4 demonstrates low pH exacerbates the effects of all HT classes. Growth rate was calculated for cells growing in SynH and SynH –HTs at pH 4.5, 5.0, and 5.5 in (A) HTsensitive strain K11 (Sake) and (B) HT-resistant strain YPS128 (NA). The average and standard deviation of growth rates measured in four biological replicates is shown. Statistically significant differences for each HT group at pH 4.5 versus 5.0 are shown with an asterisk, and differences between pH 5.0 versus 5.5 are indicated with a diamond (p<0.01, T-test)

In the course of testing the effect of amino acids, the inventors found that strains were more sensitive to HTs at lower pH. This synergistic response is known for weak acids, which are significantly more toxic at low pH because protonated acids diffuse readily into the cell (8). To test the pH effects on other compounds, the inventors divided the HT cocktail into three groups consisting of the amides, weak acids, or aldehydes (Supplementary Table S2) and tested their inhibitory effect at pH 4.5, 5.0, or 5.5 in HT-sensitive K11 and HT-resistant YPS128. The inventors found that low pH exacerbated the effects of all three HT classes (FIG. 4), particularly for the HT-sensitive K11 strain (FIG. 4A). In contrast, increasing pH above the normal pH of SynH improved tolerance to weak acids and to aldehydes, but not to amides. The pH effect was strongest when cells were exposed to the complete HT cocktail, which showed the greatest synergistic interaction with low pH, especially in HT-tolerant strain YPS128 (FIG. 4B). Thus, pH has a potent synergistic interaction with all three classes of HTs.

Genes Responding Specifically to HTs Implicate Diverse Defense Strategies

To explicitly identify gene expression changes to HTs, the inventors compared the transcriptome response to SynH directly to the response to SynH −HTs across the six strains. This identified 226 genes that were differentially expressed in one more strains, specifically in response to the toxin cocktail. From those genes, 149 were differentially expressed independent of the strain, while 119 genes were influenced by strain-by media interaction (FDR<0.01).

Among the induced genes were targets of the oxidant-induced transcription factors Yap1 (P=1.5e−14) and Skn7 (P=7.4e−5), consistent with the notion of redox stress induced by the HTs cocktail. Many of the other induced genes include those that are induced in response to a broad array of stresses (33). These included genes encoding heat shock proteins and genes responding to high osmolarity, cell wall integrity, DNA damage response, and organic solvent stress. Consistently, induced genes were enriched for known targets of the general stress transcription factor Msn2 that responds to a wide array of stresses (P=0.0014). The induced gene set also included several genes that are implicated in the reduction of HTs into less toxic compounds, and these included aldehyde reductases and dehydrogenases, aryl alcohol dehydrogenases known to be involved in oxidative stress response (36), an alpha-keto amide reductase most likely responding to the toxic amides in the HTs cocktail, and plasma membrane transporters involved in toxin transport among others (Table 3).

Figure 5:
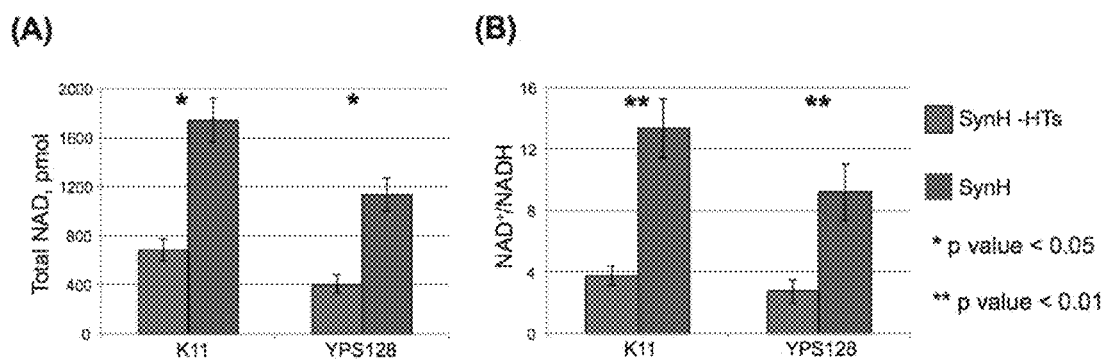
FIG. 5 illustrates NAD levels change in response to HT exposure. (A) The average and standard deviation of total NAD+/H and (B) the ratio of NAD+ to NADH are shown for HT-sensitive K11 (Sake) and HT-resistant YPS128 (NA). Data represent the average of biological triplicates and asterisks indicate statistical differences between SynH and SynH –HTs (*p<0.05, **p<0.01, Ttest).

Interestingly, genes related to thiamine metabolism were enriched (P=0.000123) in the set of HT-responsive genes having lower expression in several strains. These included four genes involved in thiamine biosynthesis (Thi2, Thi6, Thi20, Thi21) and two genes involved in thiamine uptake (Thi7, Thi73). Thiamine is important for sugar fermentation (37) and has also been shown to play a role in the defense against oxidative and osmotic stress in S. cerevisiae (38), thus this result was unexpected. Recently, it was discovered that the expression of thiamine genes can respond to NAD+ levels (39), since NAD+ is a precursor for de novo thiamine production (40). The inventors reasoned that the response of thiamine genes could reflect fluctuations in NAD+/NADH levels during HTs detoxification. The inventors quantified NAD+/NADH in the absence and presence of HTs. Strikingly, the inventors found that total NAD+ plus NADH (NAD+/H) levels (FIG. 5A) as well as the NAD+/NADH ratio (FIG. 5B) increased in the presence of HTs. This was true for both the resistant strain YPS128 and the sensitive K11 strain, although the effect was greater in K11. Interestingly, genes involved in de novo biosynthesis of NAD+ were also induced by the presence of HTs. Together, these results suggest that cells increase levels of NAD+/H in the presence of toxins, perhaps reflecting a defect in NADH regeneration during the course of detoxification.

Identifying Genes Whose Expression Correlates with HT Resistance Across Strains

Figure 6:
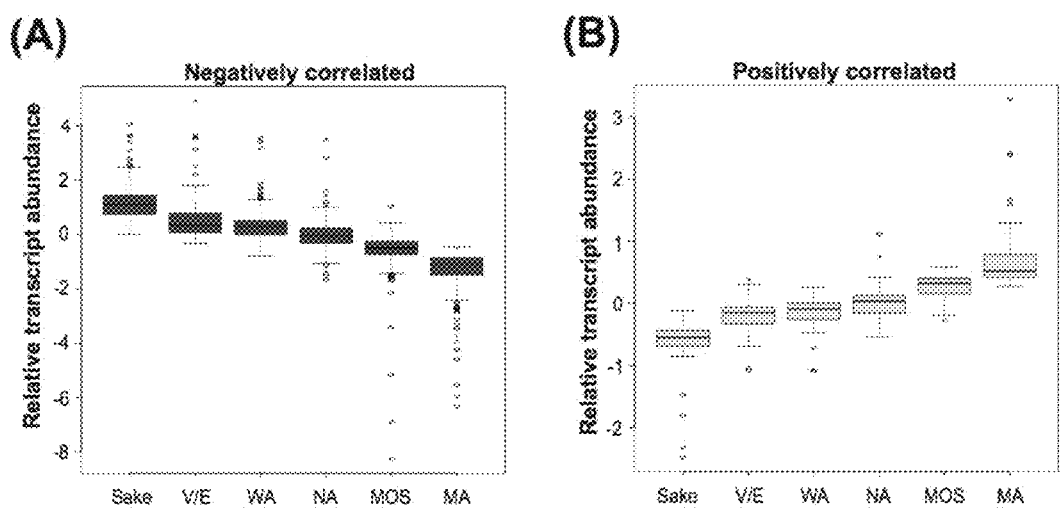
FIG. 6 illustrates identifying expression differences that correlate with HT resistance. Boxplots showing the distribution of relative transcript abundances (measured in each strain and compared to the mean expression of that gene across all strains). Shown are (A) 253 genes whose transcript abundance are negatively correlated and (B) 32 genes whose abundance is positively correlated with strain resistant scores. Strains are organized according to least (left) to highest (right) resistance.
Figure 10:
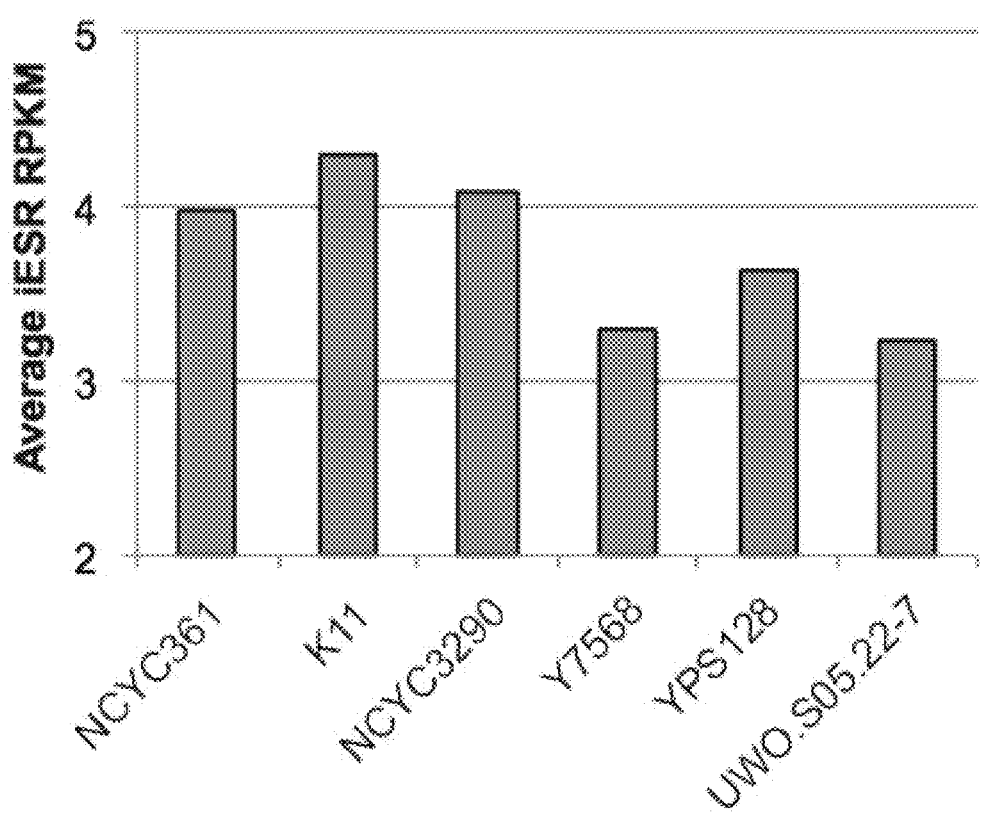
FIG. 10 shows how sensitive strains showed higher induction of ESR genes. The average transcript abundance (log 2(RPKM) values) of genes induced in the ESR are shown for listed strains.

The inventors were especially interested in exploiting the physiological differences between resistant and sensitive strains to find novel genes and mechanisms that could increase SynH tolerance. The inventors therefore identified genes whose expression level was correlated with toxin tolerance (see Methods). This identified 253 genes whose expression was negatively correlated with HT resistance (FIG. 6A) and 32 genes whose transcript abundance was positively correlated with HT resistance (FIG. 6B). The genes whose transcript abundance was negatively correlated with HT resistance—meaning that they were expressed proportionately higher as HT tolerance decreased—suggested cellular targets of the toxins. Although enrichment did not pass stringent bonferroni correction, 21% of these genes encode proteins localized in the mitochondria (uncorrected $p=0.0006$). This group included other genes involved in cell wall organization, fatty acid metabolic process, DNA repair, protein folding, and genes involved in NAD biosynthesis. The stronger expression response in HT-sensitive strains suggests that cells experiencing stronger HT stress may struggle more to maintain critical processes. Consistent with this notion, sensitive cells generally showed higher expression of genes induced in the Environmental Stress Response than tolerant cells (FIG. 10). In contrast, genes whose expression was positively correlated with HT resistance were enriched for translation (uncorrected $p=1.4e-7$), suggesting that resistant cells may be growing better under these conditions.

Other genes whose expression was positively correlated with HT resistance were involved in fatty acid elongation (uncorrected $p=6.8e-5$), amino acid transmembrane transport (uncorrected $p=0.005$), and degradation of arginine (uncorrected $p=2.2e-5$).

Fitness Effects of Gene Overexpression are Influenced by Genetic Background

The inventors were particularly interested in identifying and testing genes whose overexpression improved HT tolerance. To do this, the inventors measured changes to cellular fitness due to high-copy expression of each of 4,282 genes, using 'bar-seq' analysis of a high-copy gene library expressed in three different strains (YPS128, NCYC3290, and K11) growing in media with HTs (see Methods).

Figure 11:
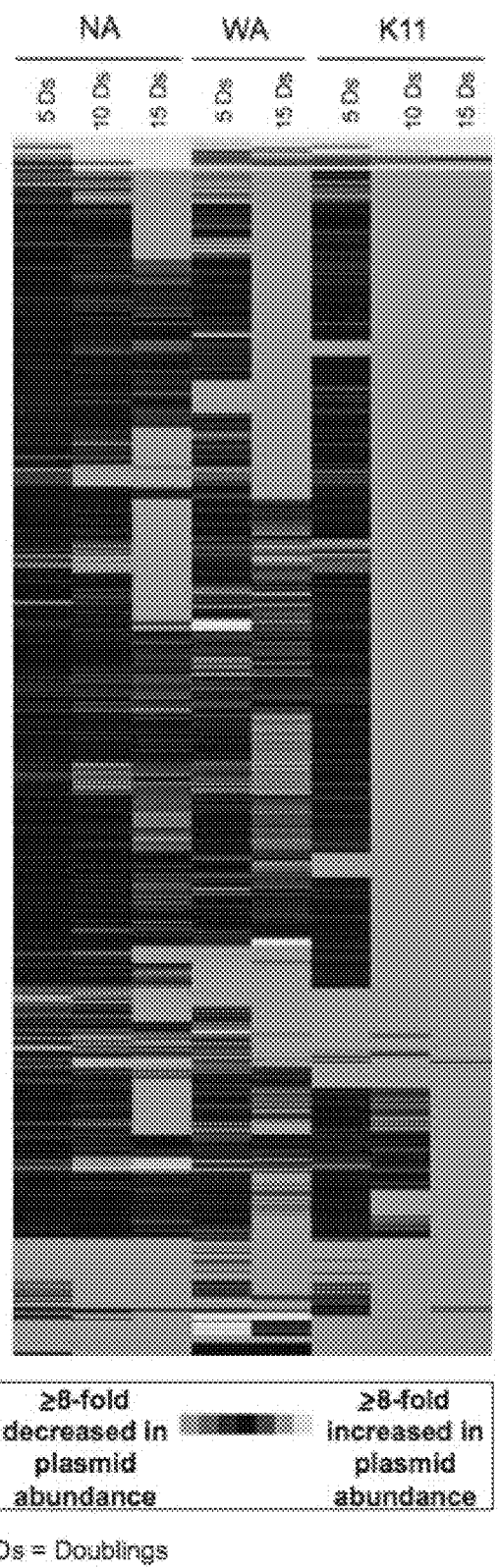
FIG. 11 depicts strain-specific responses to gene overexpression. Shown is the combined set of genes that when over expressed in NA (YPS128), WA (NCYC3290), and K11 caused a significant (FDR<0.01) fitness effect. In blue are gene-plasmids that decreased in abundance compared to the initial unselected pool, while in yellow are gene-plasmids that increased in abundance overtime compared to the initial pool.

The effects of gene overexpression were significantly influenced by genetic background (FIG. 11). Of all genes that increased fitness in SynH in any strain, only 32% (28 genes) were common in all three strains. These were weakly enriched for genes annotated in mRNA localization (uncorrected $P=0.001$) and cellular carbohydrate metabolic process (uncorrected $P=0.002$) (FIG. 7A). Somewhat surprisingly, the tolerant strain YPS128 showed fitness increases in response to the greatest number of overexpressed genes (which together had weak enrichment for genes encoding membrane proteins, uncorrected $P=0.006$), while the sensitive sake strain was influenced by only a single strain-specific gene (DBP2, whose functions involved mRNA decay and rRNA processing (41, 42), although the inventors cannot exclude that these trends are not influenced by differences in statistical power (see Methods). Interestingly, the sensitive sake strain showed a fitness defect in response to overexpression of a large number of genes (FIG. 7B), with weak enrichment for GTPase activator activity (un-corrected $P=0.0003$), SNARE binding (un-corrected $P=0.0005$), and ubiquitin-protein ligase activity (un-corrected $P=0.0005$). The extensive differences in fitness contributions depending on strain background highlights that strategies for engineering tolerance to a complex stress such as the ones found in SynH may require strain-specific strategies. Interestingly, there was no statistically significant overlap in the high-copy genes that contributed fitness benefits to one or more strains and genes that showed significant expression differences across strains. 2 out of 28 genes identified in the overexpression study had a significant expression change specifically in response to HTs.

Figure 7:
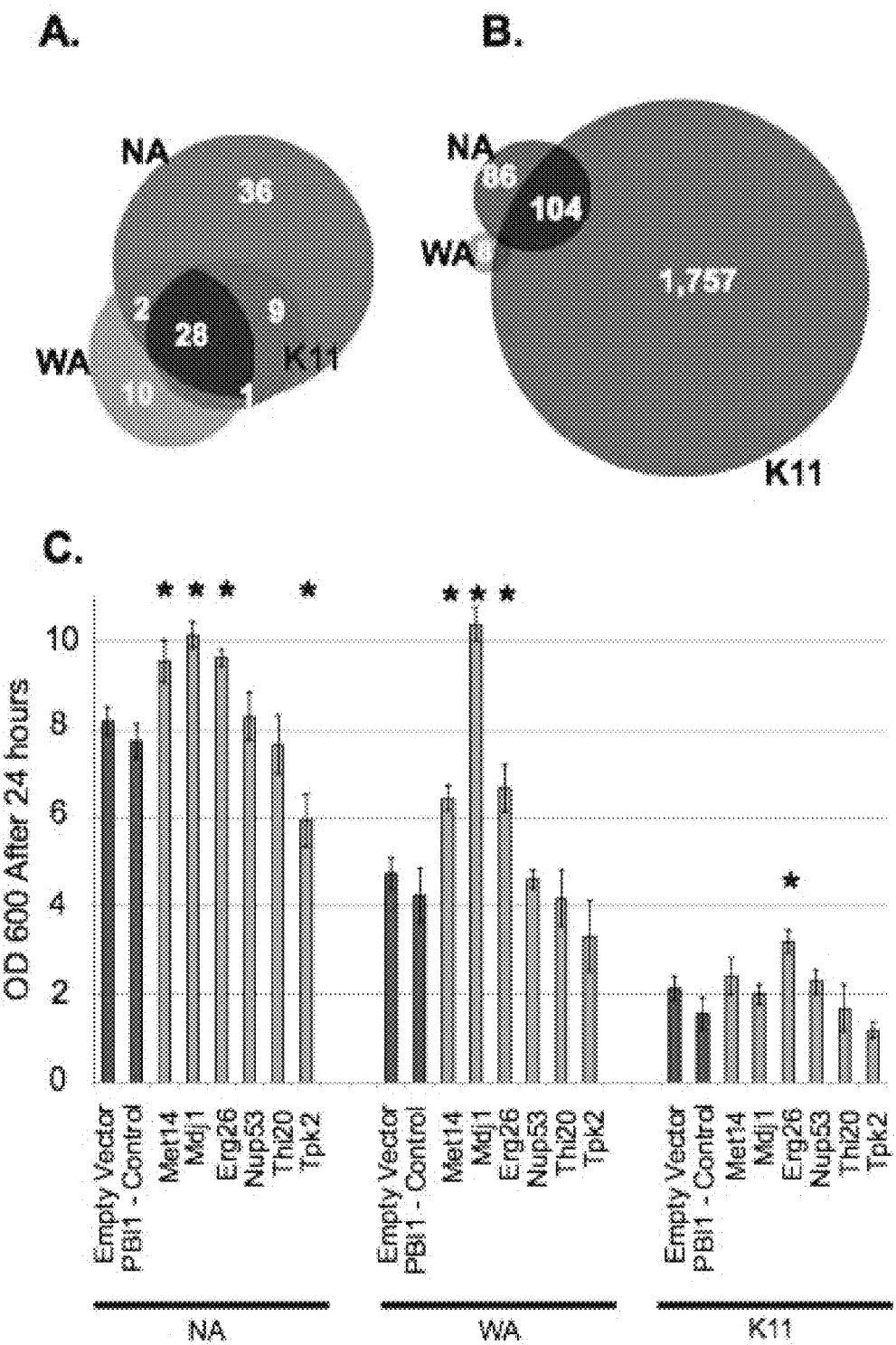
FIG. 7 depicts how gene overexpression affects HT tolerance. (A, B) The number of genes whose overexpression affected strain fitness (FDR<0.01, see Methods) is shown. (A) Genes that increased and (B) decreased fitness in YPS128 (NA), NCYC3290 (WA) or K11 are represented in the Venn diagram. (C) Final cell density after 24 h growth of denoted strains and overexpression constructs for cells growing in synthetic complete medium with high sugar content and HTs. Measurements represent the average and standard deviation of biological triplicates. Asterisks indicate statistical differences between Empty vector and gene overexpression (*p<0.01, Ttest).
Figure 8:
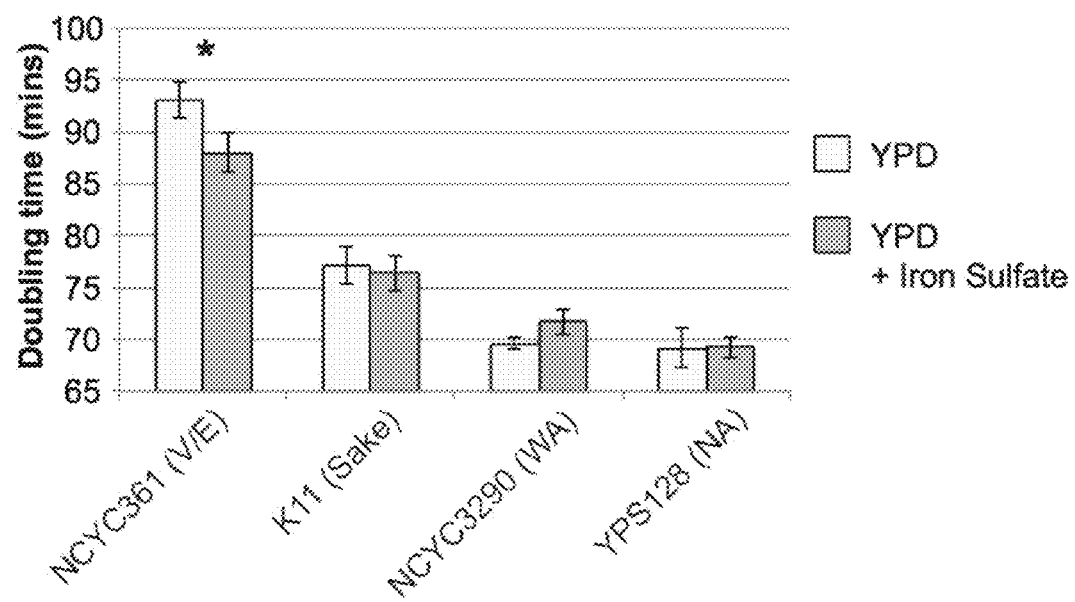
FIG. 8 shows how iron supplementation benefits NCYC361. Shown are the average and standard deviation of the doubling times measured for each strain in YPD and in YPD supplemented with 100 mg/L of iron sulfate. The doubling time was faster in NCYC361 when medium was supplemented with iron (p<0.0008, T-test) but not significantly different for any other strain. Data represent three biological replicates.

The inventors confirmed the library results by measuring fitness of cells expressing individual plasmids, compared to the empty-vector control (FIG. 7B). The inventors chose three genes identified in all strains (MET14, THI20, ERG26), two genes identified in two of the strains (MDJ1, identified in YPS128 and NCYC3290, and TPK2, identified in YPS128 and K11), and one gene (NUP53) specific to the tolerant strain YPS128. MET14 and THI20 were identified as having differential expression in HT presence (FIG. 7). The inventors also included as a control one gene (PBI1) whose expression was not predicted to change fitness. Among the six tested genes, three of them (MET14, ERG26, and MDJ1) significantly improved growth in at least two strains. The most striking was MDJ1, involved in protein folding/refolding in the mitochondrial matrix (43), which improved growth 118% in NCYC3290 and 28% in the already-tolerant YPS128. Most of the genes did not provide a strong benefit over the empty vector in K11; however, the strong negative impact of thousands of genes in the library suggests that this strain has a competing fitness deficit due to protein overexpression. The inventors note that this assay, comparing the effects of individual plasmids to the empty-vector control, is different from the competitive library experiment, in which each gene's fitness contribution is effectively normalized to the average of all plasmids (see Methods).

Discussion

In real industrial fermentations, multiple distinct stresses can have compounded effects that produce unique challenges for cells. How these different stressors interact with one another can be difficult to discern, especially in real hydrolysates that can vary extensively from batch-to-batch and according to the biomass type and source (44, 45). Furthermore, the response can be quite different depending on the genetic background of the strain. These distinctions present challenges from an industrial standpoint, especially in terms of identifying general mechanisms to improve tolerance to industrial stresses.

Our strategy to leverage natural variation, both to understand stressors in lignocellulosic hydrolysate and to identify high-impact genes for directed engineering, presents a useful strategy to tackle these hurdles. Responses common to all strains implicated the imposing stresses in SynH, including osmotic stress from the high sugar concentrations, oxidative stress produced by several HTs (46, 47), and redox imbalance, perhaps due to HT detoxification (48, 49). In contrast, responses that were graded with HT sensitivity implicate downstream cellular targets at greatest risk. For example, sensitive strains displayed stronger expression changes at genes involved in cell wall organization, fatty acid metabolism, DNA repair, protein folding, suggesting that the cell wall, membranes, the genome and proteome are primary targets of the reactants in the HT cocktail (12, 17, 49, 50). The more sensitive strains also had stronger induction of genes involved in energy generation, suggesting a tax on the energy balance (48, 51, 52). Our results also implicate a variety of defense strategies, including toxin reduction, redox defense, and drug efflux and detoxification. Several of these strategies required NADH (53-58), which likely contributes to the observed increase in NAD+/H and the NAD+/NADH ratio across strains (a response also seen in *Escherichia coli* growing in SynH (51)).

Comparing strain responses under different situations also revealed new insights into synergistic stress interactions. HT sensitivity was exacerbated at low pH, expanding the know synergy between pH and weak acids (8) to interactions with other HTs and in particular the full HT cocktail. Several expression responses to SynH –HT were exacerbated by the addition of HTs. In some cases, dual stressors may exacerbate a single cellular challenge. For example, the amplified induction of sulfur biosynthesis genes when HTs are added to the base medium may be a response to NADPH depletion, since both HT detoxification and sulfur assimilation consume NADPH (13, 14, 59). Notably, sulfate genes are also induced in bacteria growing in the presence of furfural (59) and in SynH (51). In other cases, the synergy may emerge because the defense strategy against one stress renders cells more sensitive to a second stressor. For example, cells growing in high-osmolarity SynH –HTs induced expression of osmo-induced Sko1 targets (60) and decreased expression of ergosterol biosynthesis genes. Decreased ergosterol is a physiologically adaptation to osmotic stress that may help to decrease membrane fluidity (61-63). However, reduced ergosterol is associated with lower resistance to vanillin (64); thus, altered ergosterol content could produce antagonistic effects on tolerance to osmolarity versus HTs. It is particularly interesting that genes related to two of these interactions—adenylylsulfate kinase MET14 required for sulfur assimilation and ERG26 involved in ergosterol synthesis—improve HT tolerance in the context of high sugar concentrations, in all three strains tested.

It is well known in the industry that engineering strategies are strain specific (65, 66); yet most investigations fail to consider this when identifying new engineering targets and instead focus on a single, often laboratory, strain. Our approach to examine multiple strains that together maximize genetic and phenotypic diversity not only implicated genes with background-independent benefits, but also uncovered the breadth of responses in the species. Over half the mRNAs in the transcriptome varied in abundance across strains, in one or more conditions. In several cases, the inventors were able to predict and validate cellular phenotypes based on transcriptomic differences demonstrating how far knowledge of yeast gene functions has progressed in terms of predictive power. But in other ways, our results highlight the limitations in understanding the interaction between genotype and phenotype. This is particularly true in the case of high-copy gene expression, whose differential effects suggest that background effects will be the norm rather than the exception. Our work sets the stage for more detailed mapping of phenotypic variation across strain backgrounds.

Materials and Methods
Strains and Growth Condition

Strains and phenotypes are listed in Table 1. The SynH media mimics ACSH with 90 g glucan/L loading and was prepared as in Serate et al. (2015) except that all concentrations were increased 1.5-fold to emulate a higher glucan loading (Table 2). Gene knockouts were generated by homologous recombination of the KAN-MX cassette into the locus of interest in a haploid version of YPS128 and verified by diagnostic PCR. Unless otherwise indicated, cultures were grown with vigorous shaking at 30° C. Where indicated, media was supplemented with iron (II) sulfate heptahydrate (Sigma-Aldrich, St. Louis, Mo.). Overexpression experiments were performed using the molecular barcoded yeast (MoBY 2.0) ORF library (67), growing cells in Synthetic Complete medium (SC) with high sugar concentrations and no ammonium to support G418 selection (68) (1.7 g/L YNB w/o ammonia sulfate and amino acids, 1 g/L monosodium glutamic acid, 2 g/L amino acid drop-out lacking leucine, 48 μg/L leucine, 90 g/L dextrose, 45 g/L xylose) along with the toxin cocktail (Table 4).

TABLE 1

| Strain | Strain source category | Location of isolation | HT relative growth rate |
| --- | --- | --- | --- |
| NCY3455 | Clinical | Newcastle, UK | 5 |
| K9 | Sake | Japan | 10 |
| UC5 | Sake | Kurashi, Japan | 15 |
| Y2189 | Natural Isolate | San Jacinto, California, USA | 24 |
| K10 | Sake | Japan | 26 |
| NCYC361 | Other Fermentation | NA | 29 |
| YJM269 | Other Fermentation | NA | 30 |
| YB4082 | Natural Isolate | Philippines | 31 |
| Y1 | Natural Isolate | NA | 32 |
| YJM320 | Clinical | USA | 34 |
| K11 | Sake | Japan | 34 |
| K1 | Sake | Japan | 35 |
| SK1 | Lab | USA | 37 |
| YJM428 | Clinical | USA | 38 |
| 322134S | Clinical | Newcastle, UK | 38 |
| SB | Natural Isolate | Indonesia | 40 |
| YS2 | Bakery | Australia | 42 |
| NCY3290 | Other Fermentation | Indonesia | 44 |
| L-1528 | Wine fermentation | Maule Region, Chile | 47 |
| DBVPG6765 | Natural Isolate | Indonesia | 48 |
| DCM6 | Natural Isolate | Wisconsin, USA | 49 |
| Y389 | Natural Isolate | NA | 49 |
| CLIB324 | Bakery | Vietnam | 49 |
| 273614N | Clinical | Newcastle, UK | 50 |
| YPS1009 | Oak | Mettlers Woods, NJ, USA | 50 |
| CLIB382 | Other Fermentation | Ireland | 51 |
| WE372 | Wine fermentation | Cape Town, South Africa | 52 |
| YJM308 | Clinical | USA | 53 |
| M22 | Vineyard | Italy | 54 |
| T73 | Wine fermentation | Alicante, Spain | 54 |
| 378604X | Clinical | Newcastle, UK | 54 |
| DBVPG6044 | Other Fermentation | West Africa | 54 |
| DBVPG1853 | Unknown | Ethiopia | 57 |
| YJM326 | Clinical | USA | 58 |
| CBS7960 | Industrial fermentation (sugar cane) | Sau Paulo, Brazil | 58 |
| YJM978 | Clinical | Bergamo, Italy | 58 |
| YPS606 | Natural Isolate | Woodland, PA | 59 |
| Y6 | Natural Isolate | French Guiana | 59 |
| DBVPG1373 | Natural Isolate | The Netherlands | 59 |
| YJM981 | Clinical | Bergamo, Italy | 60 |
| DBVPG1788 | Natural Isolate | Turku, Finland | 60 |

TABLE 1-continued

| Strain | Strain source category | Location of isolation | HT relative growth rate |
|---|---|---|---|
| YPS163 | Oak | Pennsylvania, USA | 60 |
| YB210 | Natural Isolate | Costa Rica | 60 |
| YJM454 | Clinical | USA | 60 |
| YPS1000 | Oak | Mettlers Woods, NJ, USA | 60 |
| YIIc17_E5 | Wine fermentation | Sauternes, France | 61 |
| YJM1129 | Other Fermentation | NA | 61 |
| DBVPG1106 | Natural Isolate | Australia | 61 |
| Y2 | Other Fermentation | Trinidad | 61 |
| YJM975 | Clinical | Bergamo, Italy | 62 |
| UWOPS83-787.3 | Natural Isolate | Bahamas | 62 |
| BC187 | Other Fermentation | Napa Valley, USA | 63 |
| I14 | Vineyard | Petina, Italy | 63 |
| CLIB215 | Bakery | New Zealand | 63 |
| YS9 | Bakery | Singapore | 63 |
| DCM16 | Natural Isolate | Wisconsin, USA | 63 |
| Y3 | Other Fermentation | Africa | 64 |
| YS4 | Bakery | The Netherlands | 64 |
| YJM339 | Clinical | USA | 64 |
| IL-01 | NA | Cahokia, IL | 64 |
| YJM421 | Clinical | USA | 64 |
| NCYC110 | Other Fermentation | West Africa | 65 |
| Y55 | Lab | NA | 65 |
| L-1374 | Wine fermentation | Maule Region, Chile | 65 |
| YPS128 | Natural Isolate | Pennsylvania, USA | 66 |
| YJM440 | Clinical | USA | 66 |
| NC-02 | Other Fermentation | Smoky Mountains, NC | 67 |
| UWOPS87-2421 | Natural isolate | Hawaii | 68 |
| Y7568 | Natural Isolate | Philippines | 68 |
| FL100 | Lab | NA | 69 |
| PW5 | Other Fermentation | Aba, Nigeria | 69 |
| PE-2 | Other Fermentation | Brazil | 69 |
| EthanolRed | Other Fermentation | NA | 70 |
| YJM653 | Clinical | NA | 71 |
| Y2209 | Natural Isolate | San Jacinto, California, USA | 72 |
| YJM451 | Clinical | Europe | 73 |
| UWOPS05-227.2 | Natural Isolate | Trigona, Malaysia | 74 |
| UWOPS05-217.3 | Natural Isolate | Malaysia | 75 |
| UWOPS03-461.4 | Natural Isolate | Malaysia | 78 |

TABLE 2

HT groups

| AMIDES | ACIDS | ALDEHYDES |
|---|---|---|
| Feruloyl amide | p-Coumaric acid | Vanillin |
| Coumaroyl amide | Ferulic acid | Syringaldehyde |
| | Benzoic acid | 4-Hydroxybenzeldehyde |
| | Syringic acid | 4-Hydroxyacetophenone |
| | Cinnamic acid | Hydroxymethyl furfural |
| | Vanillic acid | |
| | Caffeic acid | |

TABLE 3

| PROCESS | GENES |
|---|---|
| Oxidation-reductase activity | |
| Quinone reductase | ZTA1, YLR460c |
| Aldehyde reductase | ARI1 |
| Alcohol dehydrogenase | ADH7, ADH5 |
| Alpha keto amide reductase | YDL124W |
| Aryl alcohol dehydrogenase | AAD4, AAD6, AAD16 |
| Nitric oxide oxidoreductase | YHB1 |
| Oxidation of thiols | FMO1 |
| Nitroreductase | FRM2 |
| Fatty-acyl coenzyme A oxidase | POX1 |
| NADPH oxidoreductase | OYE3 |
| NADPH regeneration | YMR315W, PYC1, ZWF1 |
| de-novo NAD biosynthesis from tryptophan | BNA1, BNA5 |
| Lyase activity | |
| Decarboxylase | FDC1 |
| Plasma Membrane Transporter | |
| ABC Transporter | SNQ2, PDR12 |
| Multidrug transporter | FLR1 |

TABLE 4

SynH base media

| Component | mM Final Concentration |
|---|---|
| KH$_2$PO$_4$ | 8.76 |
| K$_2$HPO$_4$ | 16.725 |
| (NH$_4$)$_2$SO$_4$ | 45 |
| KCl | 55.2 |
| NaCl | 1.95 |
| CaCl2•2H2O | 8.25 |
| MgCl2•6H2O | 18.75 |
| L-Alanine | 1.758 |
| L-Arginine•HCl | 0.216 |
| L-Asparagine | 0.342 |
| DL-Aspartic acid•K | 0.891 |
| L-Cysteine•HCl | 0.075 |
| L-glutamine | 0.3885 |
| L-Glutamic acid•K | 0.9105 |
| Glycine | 0.567 |
| L-Histidine | 0.0561 |
| L-Isoleucine | 0.393 |
| L-Leucine | 0.5565 |
| L-Lysine•HCl | 0.2625 |
| L-Methionine | 0.15 |
| L-Phenylalanine | 0.423 |
| L-Proline | 0.984 |
| L-Serine | 0.5535 |
| L-Threonine | 0.465 |
| L-Tryptophan | 0.075 |
| L-Valine | 0.636 |
| L-Tyrosine | 0.303 |
| Adenine | 0.075 |
| Cytosine | 0.075 |
| Uracil | 0.075 |
| Guanine | 0.075 |
| Thiamine HCl | 0.0006 |
| Calcium Pantothenate | 0.0045 |
| ZnCl$_2$ | 30 |
| MnCl$_2$•4H$_2$O | 136.5 |
| CuCl$_2$•2H$_2$O | 2.85 |
| CoCl$_2$•6H$_2$O | 0.045 |
| H$_3$BO$_4$ | 34.65 |
| (NH$_4$)$_6$Mo$_7$O$_{24}$•4H$_2$O | 0.465 |
| FeCl3•6H$_2$O | 30 |
| Sodium formate | 4.2 |
| Sodium nitrate | 1.65 |
| Sodium succinate | 0.75 |
| Glycerol | 6.15 |
| Betaine•H2O | 1.05 |
| Choline Chloride | 0.45 |
| DL-Carnitine | 0.45 |
| Acetamide | 120 |
| Sodium acetate | 48 |
| L-lactatic acid (90%) | 6 |
| D-Mannose | 1.8 |
| L-Arabinose | 30 |
| D-Fructose | 36 |
| D-Galactose | 4.35 |
| D-Glucose | 90 g/l (500 mM) |
| D(+)Xylose | 45 g/l (300 mM) |

TABLE 4-continued

SynH base media

| Component | mM Final Concentration |
|---|---|
| Pyridoxine•HCl | 3.21 µM |
| Nicotinic Acid | 40.17 µM |
| Biotin | 0.15 µM |
| Inositol | 0.084 mM |
| Polysorbate 80 (Tween 80) | 1.5 ml/l |
| Ergosterol | 15 mg/l |

TABLE 5

HT cocktail

| Toxin | mM |
|---|---|
| Feruloyl amide | 8.25 |
| Coumaroyl amide | 8.25 |
| 5-Hydroxymethyl-2furadehyde | 1.65 |
| p-Coumaric acid | 3.15 |
| Ferulic acid | 1.065 |
| Benzoic acid | 0.73 |
| Syringic acid | 0.11 |
| Cinnamic acid | 0.14 |
| Vanillic acid | 0.13 |
| Caffeic acid | 0.02 |
| Vanillin | 0.20 |
| Syringaldehyde | 0.24 |
| 4-Hydroxybenzeldehyde | 0.30 |
| 4-Hydroxyacetophenone | 0.04 |

Phenotyping

10 µl of thawed frozen stock of cells was used to inoculate a 96-well plate (NUNC, Thermo Scientific, Rockford, Ill.) containing 190 µl of YPD media. Plates were sealed with breathable tape (AeraSeal, Sigma-Aldrich, St. Louis, Mo.), covered with a lid and incubated at 30° C. while shaking for 24 h, after which 10 µl of saturated cultures were used to inoculate 190 µl of YPD and grown to log phase for 6 h. Growth phenotyping was performed after inoculating 10 µl of the log phase culture into 190 µl of SynH or SynH −HTs, and growing without shaking in Tecan M200 Pro microplate reader (Tecan Systems, Inc., San Jose, Calif.) maintaining an interior chamber temperature of 30° C. Anaerobic phenotyping was performed similarly using a Tecan F500 inside an anaerobic chamber. The average of six optical density at 600 nm ($OD_{600}$) measurements distributed from across the well was taken every 30 minutes for 48 hours. Growth rates were calculated using the program GrowthRates (69). An HT resistance score was taken as the average of two biological-replicate growth rate measurements from SynH versus the average growth rates in SynH −HTs, in both aerobic and anaerobic conditions.

RNA-Seq Library Construction and Sequencing

Strains were grown in biological duplicate on different days to mid-log phase for seven generations in YPD and then shifted to YPD, SynH −HTs, or SynH medium for at least three generations to log phase (OD600 ~0.5) and collected by centrifugation. RNA was extracted by hot phenol lysis (70). Total RNA was DNAse-treated at 37° C. for 30 min with TURBO DNase (Life Technologies, Carlesbad, Calif.), followed by RNA precipitation at −20° C. in 2.5M LiCl for 30 min. rRNA depletion and library generation was via the TruSeq® Stranded Total RNA Sample Preparation Guide (Rev.C) using the Illumina TruSeq® Stranded Total RNA (Human/Mouse/Rat) kit (Illumina Inc., San Diego, Calif., USA) with minor modifications, using Agencourt RNAClean XP beads (Beckman Coulter, Indianapolis Ind., USA), SuperScript II Reverse Transcriptase (Invitrogen, Carlsbad, Calif., USA) as described in the Illumina kit. Adapter ligated DNA was amplified in a Linker Mediated PCR reaction (LM-PCR) for 12 cycles using Phusion™ DNA Polymerase and Illumina's PE genomic DNA primer set and then purified by paramagnetic beads. Libraries were standardized to 2 µM. Cluster generation was performed using standard Cluster Kits (v3) and the Illumina Cluster Station. Single-end 100 bp reads were generated using standard SBS chemistry (v3) on an Illumina HiSeq2500 sequencer. Raw data was deposited in NIH SRA database under project number GSE77505.

RNA-Seq Read Processing and Analyses

Reads were processed with Trimmomatic (71) and mapped to reference genome S288C (NC-001133, version 64 (72)) using Bowtie2 (73) with default settings. HTseq version 5.5 (74) was used to calculate read counts for each gene. Differential expression analysis was performed using the program edgeR v.3.8.6 (75) using a general linearized model with strain background and media type as factors and pairing replicate samples. Benjamini and Hochberg correction (76) was used to estimate FDR. Sequences were normalized using the reads per kilobase per million mapped reads (RPKM) method. Hierarchical clustering analysis was performed using the program Cluster 3.0 (77) and visualized with the program Java Treeview (78). Where noted, expression of each gene was normalized to the mean expression level for that gene across all strains. Functional enrichment analysis was performed using FunSpec (79, 80). All P values cited are Bonferroni-corrected, unless otherwise noted.

NAD+/NADH Measurement

Total NAD and $NAD^+$/NADH were measured in biological triplicate using Quantification Colorimetric Kit (BioVision, Milpitas, Calif.) following the recommended protocol. Briefly, strains were grown in SynH and SynH −HTs for at least three doublings, and collected while in log phase (OD600 ~0.5). NAD and NADH levels were calculated as outlined by the kit, and NAD+ was inferred from the other two measurements.

Correlations Between Expression and Toxin Tolerance

The inventors first identified 2,777 genes with significant expression differences compared to the mean expression for that gene (FDR<0.01). The inventors then averaged the replicate RPKM expression values for each strain and used Python statistical functions (SciPy.org) to calculate the Pearson correlation between each gene's expression pattern and the HT resistance scores across strains. Genes whose expression correlated with resistance were chosen based on p<0.05.

High Throughput Gene Overexpression Fitness Effects

Competition experiments were performed similar to that previously described (81, 82). Briefly, a molecular barcoded yeast ORF library (MoBY-ORF 2.0) (67, 83) was introduced into three different strains, by transforming cells with a pool library of the MoBY 2.0 collection containing 4,282 barcoded high-copy plasmids, each expressing a different yeast gene. Transformation efficiency was determined by platting serial dilutions onto YPD agar+G418-containing plates. Transformations with more than 30,000 colonies were pooled together to generate glycerol stocks used for further experiments. For competition experiments, cells were grown in SC containing monosodium glutamate as a nitrogen source and high sugar mimicking SynH (9% glucose, 4.5% xylose) plus HT cocktail and 200 mg/L of G418 (see Media) for 5, 10, and 15 generations, while maintaining cells in log phase. This medium was used instead of SynH since G418 selection required for plasmid maintenance does not function in the presence of ammonium. DNA was extracted using QIAprep Spin Miniprep kit (Qiagen, Hilden, Germany) after cell pellet pretreatment with 1 µl of RZymolyase (Zymo Research, Irvine, Calif.) and 100 µl of glass beads, with vortexing for 5 minutes. Plasmid barcodes were amplified with multiplex primers containing Illumina adapters. Barcodes of two replicates were sequenced using an Illumina HiSeq2500 Rapid Run platform. Differential abundance and significance of plasmids were determined using edgeR (75), using a linear model for each strain, identifying genes that provided a significant different fitness contribution to media +HTs compared to the starting pool before selection over time (5, 10, and 15 doublings).

REFERENCES

1. Perez J, Munoz-Dorado J, de la Rubia T, & Martinez J (2002) Biodegradation and biological treatments of cellulose, hemicellulose and lignin: an overview. *Int Microbiol* 5(2):53-63.
2. Chundawat S P, Beckham G T, Himmel M E, & Dale B E (2011) Deconstruction of lignocellulosic biomass to fuels and chemicals. *Annu Rev Chem Biomol Eng* 2:121-145.
3. Sun Y & Cheng J (2002) Hydrolysis of lignocellulosic materials for ethanol production: a review. *Bioresour Technol* 83(1):1-11.
4. Klinke H B, Thomsen A B, & Ahring B K (2004) Inhibition of ethanol-producing yeast and bacteria by degradation products produced during pre-treatment of biomass. *Appl Microbiol Biotechnol* 66(1):10-26.
5. Piotrowski J S, et al. (2014) Death by a thousand cuts: the challenges and diverse landscape of lignocellulosic hydrolysate inhibitors. *Front Microbiol* 5.
6. Larsson S, Reimann A, Nilvebrant N-O, & Jönsson L (1999) Comparison of different methods for the detoxification of lignocellulose hydrolyzates of spruce. *Applied Biochemistry and Biotechnology* 77(1-3):91-103.
7. Palmqvist E & Hahn-Hägerdal B (2000) Fermentation of lignocellulosic hydrolysates. II: inhibitors and mechanisms of inhibition. *Bioresource Technology* 74(1):25-33.
8. Ullah A, Orij R, Brul S, & Smits G J (2012) Quantitative analysis of the modes of growth inhibition by weak organic acids in *Saccharomyces cerevisiae*. *Appl Environ Microbiol* 78(23):8377-8387.
9. Russell J B (1992) Another explanation for the toxicity of fermentation acids at low pH: anion accumulation versus uncoupling. *Journal of Applied Bacteriology* 73(5):363-370.
10. Holyoak C D, et al. (1996) Activity of the plasma membrane H(+)-ATPase and optimal glycolytic flux are required for rapid adaptation and growth of *Saccharomyces cerevisiae* in the presence of the weak-acid preservative sorbic acid. *Appl Environ Microbiol* 62(9):3158-3164.
11. Modig T, Liden G, & Taherzadeh M J (2002) Inhibition effects of furfural on alcohol dehydrogenase, aldehyde dehydrogenase and pyruvate dehydrogenase. *Biochem J* 363(Pt 3):769-776.
12. Allen S A, et al. (2010) Furfural induces reactive oxygen species accumulation and cellular damage in *Saccharomyces cerevisiae*. *Biotechnol Biofuels* 3:2.
13. Diaz De Villegas M E, et al. (1992) Conversion of furfural into furfuryl alcohol by *saccharomyces cerevisiae* 354. *Acta Biotechnologica* 12(4):351-354.
14. Taherzadeh M J, Gustafsson L, Niklasson C, & Liden G (2000) Physiological effects of 5-hydroxymethylfurfural on *Saccharomyces cerevisiae*. *Appl Microbiol Biotechnol* 53(6):701-708.
15. Almeida J R M, et al. (2007) Increased tolerance and conversion of inhibitors in lignocellulosic hydrolysates by *Saccharomyces cerevisiae*. *Journal of Chemical Technology & Biotechnology* 82(4):340-349.
16. Krebs H A, Wiggins D, Stubbs M, Sols A, & Bedoya F (1983) Studies on the mechanism of the antifungal action of benzoate. *Biochemical Journal* 214(3):657-663.
17. Nguyen T T, Iwaki A, Ohya Y, & Izawa S (2014) Vanillin causes the activation of Yap1 and mitochondrial fragmentation in *Saccharomyces cerevisiae*. *J Biosci Bioeng* 117(1):33-38.
18. Chambel A, Viegas C A, & Sá-Correia I (1999) Effect of cinnamic acid on the growth and on plasma membrane H+-ATPase activity of *Saccharomyces cerevisiae*. *International Journal of Food Microbiology* 50(3):173-179.
19. Verduyn C, Postma E, Scheffers W A, & Van Dijken J P (1992) Effect of benzoic acid on metabolic fluxes in yeasts: a continuous-culture study on the regulation of respiration and alcoholic fermentation. *Yeast (Chichester, England)* 8(7):501517.
20. Pisithkul T, Jacobson T B, O'Brien T J, Stevenson D M, & Amador-Noguez D (2015) Phenolic Amides Are Potent Inhibitors of De Novo Nucleotide Biosynthesis. *Appl Environ Microbiol* 81(17):5761-5772.
21. Iwaki A, Ohnuki S, Suga Y, Izawa S, & Ohya Y (2013) Vanillin inhibits translation and induces messenger ribonucleoprotein (mRNP) granule formation in *saccharomyces cerevisiae*: application and validation of high-content, imagebased profiling. *PLoS One* 8(4):e61748.
22. Skerker J M, et al. (2013) Dissecting a complex chemical stress: chemogenomic profiling of plant hydrolysates. *Mol Syst Biol* 9:674.
23. Keating D H, et al. (2014) Aromatic inhibitors derived from ammonia-pretreated lignocellulose hinder bacterial ethanologenesis by activating regulatory circuits controlling inhibitor efflux and detoxification. *Front Microbiol* 5.
24. Warringer J, et al. (2011) Trait variation in yeast is defined by population history. *PLoS Genet* 7(6):e1002111.
25. Kvitek D J, Will J L, & Gasch A P (2008) Variations in stress sensitivity and genomic expression in diverse *S. cerevisiae* isolates. *PLoS Genet* 4(10):e1000223.
26. Liti G, et al. (2009) Population genomics of domestic and wild yeasts. *Nature* 458(7236):337-341.
27. Serate J, et al. (2015) Controlling microbial contamination during hydrolysis of AFEX-pretreated corn stover and switchgrass: effects on hydrolysate composition, microbial response and fermentation. *Biotechnology for Biofuels* 8(1):1-17.
28. Cromie G A, et al. (2013) Genomic sequence diversity and population structure of *Saccharomyces cerevisiae* assessed by RAD-seq. *G3 (Bethesda)* 3(12):2163-2171.
29. Strope P K, et al. (2015) The 100-genomes strains, an *S. cerevisiae* resource that illuminates its natural phenotypic and genotypic variation and emergence as an opportunistic pathogen. *Genome Res* 25(5):762-774.
30. Clowers K J, Heilberger J, Piotrowski J S, Will J L, & Gasch A P (2015) Ecological and Genetic Barriers Differentiate Natural Populations of *Saccharomyces cerevisiae*. *Mol Biol Evol* 32(9):2317-2327.
31. Cubillos F A, et al. (2011) Assessing the complex architecture of polygenic traits in diverged yeast populations. *Mol Ecol* 20(7):1401-1413.

32. Sherman F (1991) Getting started with yeast. *Methods Enzymol* 194(3):21.
33. Gasch A P, et al. (2000) Genomic expression programs in the response of yeast cells to environmental changes. Mol Biol Cell 11(12):4241-4257.
34. Shakoury-Elizeh M, et al. (2010) Metabolic response to iron deficiency in *Saccharomyces cerevisiae*. J Biol Chem 285(19):14823-14833.
35. Hinnebusch A G (2005) Translational regulation of GCN4 and the general amino acid control of yeast. Annu Rev Microbiol 59:407-450.
36. Delneri D, Gardner D C, & Oliver S G (1999) Analysis of the seven-member AAD gene set demonstrates that genetic redundancy in yeast may be more apparent than real. Genetics 153(4):1591-1600.
37. Hohmann S & Meacock P A (1998) Thiamin metabolism and thiamin diphosphate-dependent enzymes in the yeast *Saccharomyces cerevisiae*: genetic regulation. Biochimica et biophysica acta 1385(2):201-219.
38. Wolak N, Kowalska E, Kozik A, & Rapala-Kozik M (2014) Thiamine increases the resistance of baker's yeast *Saccharomyces cerevisiae* against oxidative, osmotic and thermal stress, through mechanisms partly independent of thiamine diphosphate-bound enzymes. FEMS Yeast Res 14(8):1249-1262.
39. Li M, et al. (2010) Thiamine biosynthesis in *Saccharomyces cerevisiae* is regulated by the NAD+-dependent histone deacetylase Hst1. Mol Cell Biol 30(13):3329-3341.
40. Chatterjee A, Jurgenson C T, Schroeder F C, Ealick S E, & Begley T P (2007) Biosynthesis of thiamin thiazole in eukaryotes: conversion of NAD to an advanced intermediate. J Am Chem Soc 129(10):2914-2922.
41. Barta I & Iggo R (1995) Autoregulation of expression of the yeast Dbp2p 'DEADbox' protein is mediated by sequences in the conserved DBP2 intron. *EMBO J* 14(15):3800-3808.
42. Bond A T, Mangus D A, He F, & Jacobson A (2001) Absence of Dbp2p alters both nonsense-mediated mRNA decay and rRNA processing. Mol Cell Biol 21(21):7366-7379.
43. Rowley N, et al. (1994) Mdj1p, a novel chaperone of the DnaJ family, is involved in mitochondrial biogenesis and protein folding. Cell 77(2):249-259.
44. Chundawat S P, et al. (2010) Multifaceted characterization of cell wall decomposition products formed during ammonia fiber expansion (AFEX) and dilute acid based pretreatments. Bioresour Technol 101.
45. Bunnell K, et al. (2013) Plant Maturity Effects on the Physicochemical Properties and Dilute Acid Hydrolysis of Switchgrass (*Panicum virgatum*, L.) Hemicelluloses. ACS Sustainable Chemistry & Engineering 1(6):649-654.
46. Guo Z & Olsson L (2014) Physiological response of *Saccharomyces cerevisiae* to weak acids present in lignocellulosic hydrolysate. *FEMS Yeast Res* 14(8):1234-1248.
47. Liu Z L (2011) Molecular mechanisms of yeast tolerance and in situ detoxification of lignocellulose hydrolysates. *Appl Microbiol Biotechnol* 90(3):809-825.
48. Gorsich S W, et al. (2006) Tolerance to furfural-induced stress is associated with pentose phosphate pathway genes ZWF1, GND1, RPE1, and TKL1 in *Saccharomyces cerevisiae*. Appl Microbiol Biotechnol 71(3):339-349.
49. Ma M & Liu Z L (2010) Comparative transcriptome profiling analyses during the lag phase uncover YAP1, PDR1, PDR3, RPN4, and HSF1 as key regulatory genes in genomic adaptation to the lignocellulose derived inhibitor HMF for *Saccharomyces cerevisiae*. BMC Genomics 11:660.
50. Lin F M, Qiao B, & Yuan Y J (2009) Comparative proteomic analysis of tolerance and adaptation of ethanologenic *Saccharomyces cerevisiae* to furfural, a lignocellulosic inhibitory compound. Appl Environ Microbiol 75(11):3765-3776.
51. Keating D H, et al. (2014) Aromatic inhibitors derived from ammonia-pretreated lignocellulose hinder bacterial ethanologenesis by activating regulatory circuits controlling inhibitor efflux and detoxification. Front Microbiol 5:402.
52. Liu Z L, Ma M, & Song M (2009) Evolutionarily engineered ethanologenic yeast detoxifies lignocellulosic biomass conversion inhibitors by reprogrammed pathways. Mol Genet Genomics 282(3):233-244.
53. Liu Z L, et al. (2004) Adaptive response of yeasts to furfural and 5hydroxymethylfurfural and new chemical evidence for HMF conversion to 2,5bis-hydroxymethylfuran. *J Ind Microbiol Biotechnol* 31(8):345-352.
54. Nilsson A, Gorwa-Grauslund M F, Hahn-Hagerdal B, & Liden G (2005) Cofactor dependence in furan reduction by *Saccharomyces cerevisiae* in fermentation of acid-hydrolyzed lignocellulose. Appl Environ Microbiol 71(12):7866-7871.
55. Petersson A, et al. (2006) A 5-hydroxymethyl furfural reducing enzyme encoded by the *Saccharomyces cerevisiae* ADH6 gene conveys HMF tolerance. Yeast (Chichester, England) 23(6):455-464.
56. Liu Z L & Moon J (2009) A novel NADPH-dependent aldehyde reductase gene from *Saccharomyces cerevisiae* NRRL Y-12632 involved in the detoxification of aldehyde inhibitors derived from lignocellulosic biomass conversion. Gene 446(1):1-10.
57. Almeida J R, et al. (2008) NADH- vs NADPH-coupled reduction of 5hydroxymethyl furfural (HMF) and its implications on product distribution in *Saccharomyces cerevisiae*. Appl Microbiol Biotechnol 78(6):939-945.
58. Liu Z L, Moon J, Andersh B J, Slininger P J, & Weber S (2008) Multiple genemediated NAD(P)H-dependent aldehyde reduction is a mechanism of in situ detoxification of furfural and 5-hydroxymethylfurfural by *Saccharomyces cerevisiae*. Appl Microbiol Biotechnol 81(4):743-753.
59. Miller E N, et al. (2009) Furfural inhibits growth by limiting sulfur assimilation in ethanologenic *Escherichia coli* strain LY180. *Appl Environ Microbiol* 75(19):6132-6141.
60. Proft M, et al. (2001) Regulation of the Sko1 transcriptional repressor by the Hog1 MAP kinase in response to osmotic stress. *EMBO* 20(5):1123-1133.
61. Montanes F M, Pascual-Ahuir A, & Proft M (2011) Repression of ergosterol biosynthesis is essential for stress resistance and is mediated by the Hog1 MAP kinase and the Mot3 and Rox1 transcription factors. Mol Microbiol 79(4):10081023.
62. Rodriguez-Vargas S, Sanchez-Garcia A, Martinez-Rivas J M, Prieto J A, & Randez-Gil F (2007) Fluidization of membrane lipids enhances the tolerance of *Saccharomyces cerevisiae* to freezing and salt stress. Appl Environ Microbiol 73(1):110-116.
63. Abe F & Hiraki T (2009) Mechanistic role of ergosterol in membrane rigidity and cycloheximide resistance in *Saccharomyces cerevisiae*. Biochimica et biophysica acta 1788(3):743-752.

64. Endo A, Nakamura T, & Shima J (2009) Involvement of ergosterol in tolerance to vanillin, a potential inhibitor of bioethanol fermentation, in *Saccharomyces cerevisiae*. *FEMS Microbiol Lett* 299(1):95-99.
65. Kasavi C, et al. (2012) Evaluation of industrial *Saccharomyces cerevisiae* strains for ethanol production from biomass. Biomass and Bioenergy 45:230238.
66. Le Borgne S (2012) Genetic engineering of industrial strains of *Saccharomyces cerevisiae*. Methods Mol Biol 824:451-465.
67. Ho C H, et al. (2009) A molecular barcoded yeast ORF library enables mode-ofaction analysis of bioactive compounds. Nat Biotechnol 27(4):369-377.
68. Xiao W (2006) Yeast protocols (Springer).
69. Hall B G, Acar H, Nandipati A, & Barlow M (2014) Growth rates made easy. Mol Biol Evol 31(1):232-238.
70. Gasch A P (2002) Yeast genomic expression studies using DNA microarrays. Methods Enzymol 350:393-414.
71. Bolger A M, Lohse M, & Usadel B (2014) Trimmomatic: a flexible trimmer for Illumina sequence data. Bioinformatics 30(15):2114-2120.
72. Engel S R, et al. (2014) The reference genome sequence of *Saccharomyces cerevisiae*: then and now. *G3 (Bethesda)* 4(3):389-398.
73. Langmead B & Salzberg S L (2012) Fast gapped-read alignment with Bowtie 2. Nat Methods 9(4):357-359.
74. Anders S, Pyl P T, & Huber W (2015) HTSeq—a Python framework to work with high-throughput sequencing data. Bioinformatics 31(2):166-169.
75. Robinson M D, McCarthy D J, & Smyth G K (2010) edgeR: a Bioconductor package for differential expression analysis of digital gene expression data. Bioinformatics 26(1):139-140.
76. Benjamini Y & Hochberg Y (1995) Controlling the False Discovery Rate: A Practical and Powerful Approach to Multiple Testing. *Journal of the Royal Statistical Society. Series B (Methodological)* 57(1):289-300.
77. Eisen M B, Spellman P T, Brown P O, & Botstein D (1998) Cluster analysis and display of genome-wide expression patterns. *Proc Natl Acad Sci USA* 95(25): 14863-14868.
78. Saldanha A J (2004) Java Treeview—extensible visualization of microarray data. Bioinformatics 20(17):3246-3248.
79. Robinson M D, Grigull J, Mohammad N, & Hughes T R (2002) FunSpec: a webbased cluster interpreter for yeast. BMC Bioinformatics 3:35.
80. Boyle E I, et al. (2004) GO::TermFinder—open source software for accessing Gene Ontology information and finding significantly enriched Gene Ontology terms associated with a list of genes. Bioinformatics 20(18):3710-3715.
81. Piotrowski J S, et al. (2015) Chemical genomic profiling via barcode sequencing to predict compound mode of action. *Methods Mol Biol* 1263:299-318.
82. Magtanong L, et al. (2011) Dosage suppression genetic interaction networks enhance functional wiring diagrams of the cell. *Nat Biotechnol* 29(6):505-511.
83. Ho C H, et al. (2011) Combining functional genomics and chemical biology to identify targets of bioactive compounds. *Curr Opin Chem Biol* 15(1):66-78.

As can be appreciated, the results described in the above examples support the utility of the nucleic acids, yeast strains and methods described and claimed herein for enhancing biofuel production in yeast. Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific materials, methods, formulations, reaction/assay conditions, etc., herein illustrated and described, but embraces such modified forms thereof as come within the scope of the following claims.

What is claimed is:

1. A recombinant vector comprising: (a) the nucleotide sequence of SEQ ID NO:1, SEQ ID NO:2, or SEQ ID NO:3; and (b) a promoter operably-linked to the nucleotide sequence of (a); wherein overexpression in yeast of said nucleotide sequence provides increased tolerance to lignocellulosic toxins relative to a control yeast lacking overexpression of the nucleotide sequence.

2. The recombinant vector of claim 1, wherein said vector includes heterologous nucleotide sequences that stably maintain the vector at a high copy number when transformed into yeast.

3. The recombinant vector of claim 1, wherein the promoter is a heterologous promoter.

4. A recombinant yeast comprising the recombinant vector of claim 1.

5. The recombinant yeast of claim 4, wherein the recombinant yeast is of the genus *Saccharomyces*.

6. The recombinant yeast of claim 5, wherein the recombinant yeast is of the species *Saccharomyces cerevisiae*.

7. The recombinant yeast of claim 4, wherein the recombinant vector is an extrachromosomal vector stably maintained in the recombinant yeast.

8. The recombinant yeast of claim 4, wherein the recombinant vector is stably maintained at a high copy number in the recombinant yeast.

9. The recombinant yeast of claim 4, wherein the recombinant vector is integrated into a chromosome of the recombinant yeast.

10. A recombinant *Saccharomyces cerevisiae* strain, comprising: an isolated nucleotide sequence encoding and overexpressing an adenylylsulfate kinase (MET14), protein folding protein folding co-chaperone (MDJ1), or C3 sterol dehydrogenase (ERG26); wherein the isolated nucleotide sequence is contained in an extrachromosomal vector maintained at a high copy number in the strain, and said strain exhibits increased tolerance to lignocellulosic toxins relative to a control strain lacking the isolated nucleotide sequence.

* * * * *

SEQUENCE LISTING

```
<160> NUMBER OF SEQ ID NOS: 6

<210> SEQ ID NO 1
<211> LENGTH: 609
<212> TYPE: DNA
<213> ORGANISM: Saccharomyces cerevisiae

<400> SEQUENCE: 1
atggctacta atattacttg gcatccaaat cttacttacg acgaacgcaa ggcattgaga      60
aaacaggacg gttgtactat ttggttaaca ggtctaagtg cgtcaggtaa aagtacaatc     120
gcctgtgcgc tagaacagtt actgctccaa aaaaacttgt ctgcatatag attggatggt    180
gacaacattc gttttggatt gaacaaggat ttgggtttct cagaaaagga cagaaatgaa    240
aacattcgta gaattagcga agtttctaag ctatttgctg attcatgtgc tatttcaatc    300
acctcattta tctctccata cagagttgac agagatagag ctcgtgaact acataaggag    360
gctggtttga agttcattga aatatttgtt gatgttccat tagaagtcgc tgagcaaagg    420
gaccctaagg gtttatacaa gaaagctagg gagggtgtaa tcaaggagtt tacaggtatt    480
tctgccccat atgaagcgcc aaaagctcca gagctacatt tgagaaccga ccagaagacg    540
gttgaagaat gtgctaccat tatttatgag tacttaatca gtgaaaaaat catccgtaag    600
catttgtaa                                                            609
```

<210> SEQ ID NO 2
<211> LENGTH: 1536
<212> TYPE: DNA
<213> ORGANISM: Saccharomyces cerevisiae

<400> SEQUENCE: 2

| | | | | | | |
|---|---|---|---|---|---|---|
| atggctttcc | aacaaggtgt | attgtcaagg | tgttccggtg | tctttagaca | ccatgtggga | 60 |
| cattctcgcc | atatcaataa | tattctttat | agacatgcca | tcgcgtttgc | atccatcgct | 120 |
| ccacgaatac | caaaatctag | cttccatact | tctgcaatca | gaaacaacga | agcattcaag | 180 |
| gacccgtacg | atactttagg | cttgaagaaa | tctgctacag | gtgcggaaat | caaaaaagca | 240 |
| tactacaaac | tggcaaagaa | gtaccacccg | gatatcaaca | aggaaccgga | tgctgagaag | 300 |
| aaattccacg | atttacagaa | cgcttatgaa | attctgtcag | acgaaacgaa | gaggcagcag | 360 |
| tacgatcaat | ttgggcccgc | tgccttcggc | ggcggcggtg | ccgctggagg | tgccggtggt | 420 |
| ggtagtggct | ctcccttttgg | ttcccaattt | catgatttct | caggattcac | cagtgcaggc | 480 |
| ggctcgccat | ttggcggtat | caattttgaa | gacctgtttg | gtgctgcatt | tggtggtggt | 540 |
| ggccgcggta | gcgtggcgc | aagcaggtcg | tcatctatgt | tcagacaata | taggggcgac | 600 |
| ccaatcgaga | ttgtccataa | agtgtctttc | aaggacgcag | tgtttgggtc | caagaacgtt | 660 |
| cagttaagat | tctctgcgct | ggacccttgt | agtacctgtt | cagggacggg | aatgaaacca | 720 |
| aacacgcata | aggtcagttg | tagcacttgt | cacggaacag | gaaccactgt | tcacattagg | 780 |
| ggcggatttc | agatgatgtc | gacttgtcct | acttgcaacg | gtgaaggtac | catgaaacgg | 840 |
| cctcaggaca | attgtaccaa | gtgccatggt | gagggtgttc | aggtcaacag | ggcaaagaca | 900 |
| attacggtgg | acttgccaca | tggattacag | gacggcgacg | tggtcaggat | ccctggccaa | 960 |
| ggctcatacc | ctgacatcgc | tgtagaggcg | gacttgaaag | attcagtcaa | gttatcaaga | 1020 |
| ggtgatattt | tggtgagaat | tcgtgtcgac | aaggatccca | acttttcgat | aaagaacaag | 1080 |
| tacgatattt | ggtacgacaa | ggagattcct | ataaccacag | ctgcacttgg | tggtactgtc | 1140 |
| actatcccca | ctgtgagggg | acaaaagatc | aggataaagg | tcgctccagg | gactcaatac | 1200 |
| aatcaagtga | tatccattcc | taacatgggt | gttcctaaaa | catcaaccat | tcgcggtgat | 1260 |
| atgaaagtcc | agtacaagat | cgttgttaag | aaaccgcaat | cgctggcaga | aaaatgcttg | 1320 |
| tgggaggcac | tggcagatgt | caccaacgat | gacatggcca | gaaaaccat | gcaaccgggc | 1380 |
| acagccgcgg | gtacagccat | taatgaagag | atactgaaga | aacaaaaaca | agaagaggaa | 1440 |
| aaacacgcaa | aaaaggatga | cgacaacact | ttgaagagac | tagaaaattt | cattaccaac | 1500 |
| acattcagga | agatcaaagg | tgacaaaaaa | aattaa | | | 1536 |

<210> SEQ ID NO 3
<211> LENGTH: 1050
<212> TYPE: DNA
<213> ORGANISM: Saccharomyces cerevisiae

<400> SEQUENCE: 3

| | | | | | | |
|---|---|---|---|---|---|---|
| atgtcaaaga | tagattcagt | tttaattatc | ggtggttctg | gttttcttgg | attgcactta | 60 |
| attcagcaat | tttttgatat | taatcctaag | ccagacatcc | acatttttga | tgttagagat | 120 |
| ctccctgaaa | aactttcaaa | acagtttact | tttaatgtag | acgacataaa | atttcataag | 180 |
| ggtgatttaa | catcacctga | tgatatggaa | aacgcaatta | acgaaagtaa | agcaaatgtt | 240 |
| gttgttcatt | gtgcttctcc | aatgcatggt | caaaatccag | atatttatga | catagtgaat | 300 |

```
gttaagggaa cccgtaacgt gatagatatg tgcaagaaat gtggcgttaa tatacttgta    360
tatacttcct ctgctggtgt tatttttaat gggcaagatg tgcacaatgc agacgaaacc    420
tggccaatcc cagaagttcc tatggatgcg tacaatgaga ctaaagctat cgccgaagat    480
atggtcttga aggcgaatga tccaagcagt gatttctata ctgttgctct tcgtccagct    540
ggtattttg gcccaggtga taggcaatta gtacctggtc taagacaggt tgcgaaattg    600
gggcagtcga agttccaaat tggtgataat acaatctat ttgattggac ttatgctgga    660
aatgttgctg acgcgcatgt gttagctgca cagaaacttc tcgatccaaa acaagaact    720
gctgtctcgg gtgaaacttt tttcattacc aatgataccc ccacctattt ttgggccttg    780
gcccgtactg tgtggaaggc agatggtcat attgataaac atgttattgt tttgaaaagg    840
ccagttgcaa tttgtgcagg ttatctttca gaatgggtat ccaagatgct gggtaaagag    900
ccaggtttga ctccattcag agtcaagatt gtgtgtgcat accgttatca caacattgct    960
aaggccaaaa agttgctagg ctacacacca agagttggta ttgaagaagg aattaacaaa   1020
acgttggcct ggatggacga aggtttgtaa                                     1050

<210> SEQ ID NO 4
<211> LENGTH: 1771
<212> TYPE: DNA
<213> ORGANISM: Saccharomyces cerevisiae

<400> SEQUENCE: 4
gcatttatct ttctcttgaa ccgtaaatat cattttcata agtcacatga taaaaacata     60
tttaaaattt taaaaaaatt aattttcaaa ataaatttat tatattttt taattacata    120
atcataaaaa taaatgttca tgatttccga acgtataaaa taagaatgtt acgagaattt    180
gttttcttgg taattaaaat aatcaaatac acatagaaag gagagtaaac tgcttcctct    240
gtataaatca aagcaaaatt gtaaatagcg ttgacaagtg attacagaag ttaggtgagg    300
ttaattacca atttctttttt ttaaaattgg tgaaataaga ttacgtttaa aggagcatta    360
acaggtttac tcataacaat cattttcaaa tttccctatg catgtttaga gcaagcgcct    420
ttgtgagccc tcccggttac gacgccttgg caatgtagca gataactctg cacttctaga    480
atcattccac tacgacattt ggctcatcac cagctcgcga gaaatgtaaa taagccaaca    540
accaagaatg cgtaacatta agaatacag ttgctttcat ttcggcgtga tggtacggca    600
cccacggtac cttacattat tctcgaaaaa tagctgcacg cttttccagg aataaaagac    660
cgtgccacta atttcacgtg atcaatatat ttacaagcca cctcaaaaaa tgtggcaatg    720
gagaagagga tgaacgactc aatatgactt caacttcatg aatttgtcaa atatctata     780
taagatgcaa aatttctata caacatcagt tgcgtatccg ttaatgtcgt tcattttctc    840
tctttgttcg aacttgacat caagaaaagt tggaattatt tctccaagca cactgtacac    900
caatggctac taatattact tggcatccaa atcttactta cgacgaacgc aaggcattga    960
gaaaacagga cggttgtact atttggttaa caggtctaag tgcgtcaggt aaaagtacaa   1020
tcgcctgtgc gctagaacag ttactgctcc aaaaaaactt gtctgcatat agattggatg   1080
gtgacaacat tcgtttttgga ttgaacaagg atttgggttt ctcagaaaag gacagaaatg   1140
aaaacattcg tagaattagc gaagttctct agctatttgc tgattcatgt gctatttcaa   1200
tcacctcatt tatctctcca tacagagttg acagagatag agctcgtgaa ctacataagg   1260
aggctggttt gaagttcatt gaaatatttg ttgatgttcc attagaagtc gctgagcaaa   1320
gggaccctaa gggtttatac aagaaagcta gggagggtgt aatcaaggag tttacaggta   1380
```

| | |
|---|---:|
| tttctgcccc atatgaagcg ccaaaagctc cagagctaca tttgagaacc gaccagaaga | 1440 |
| cggttgaaga atgtgctacc attatttatg agtacttaat cagtgaaaaa atcatccgta | 1500 |
| agcatttgta atttgaccga ttactgtaca tttaatgata tataaaagat gtatatatat | 1560 |
| aatatagaac atatttattc gaggattcat tcgaaaaaaa aagaaaactt tagtgacgag | 1620 |
| attgagtaaa gtgaaaaact gaacaaattt tcggaagcct tttgattcta agtgcctact | 1680 |
| ttgatatcag tagttgatgt attatagtat agacctatta ttcattaaat atactcagag | 1740 |
| cgctcaagtc tgcttcttca aagtgttcaa c | 1771 |

<210> SEQ ID NO 5
<211> LENGTH: 2629
<212> TYPE: DNA
<213> ORGANISM: Saccharomyces cerevisiae
<400> SEQUENCE: 5

| | |
|---|---:|
| cgcaattcac cgtcctattt atacgtttta atatagattt agagaaagac ctttcagatc | 60 |
| aagaggggga cgaccggaac ctcaaagttg accaaacgat tttccagggg ctgtagatct | 120 |
| agttactctc cgtctagagt gcttctggtc tgtgtttgtg ggttgtatta atgcttgcgt | 180 |
| atacctttcc ttctttcaat ttctacgtca atgggttttt ttccttcctt ttcctttttcc | 240 |
| ttttcctttt cccctcttta ctacgttttct atgttatttt gtgccgcccc ctgcaagttg | 300 |
| caacatatcc ccttaacaga tgccagcaat attctagtct tgctatttttt accgcctctg | 360 |
| gcttttggct tctagtcctt gtcccaagag ccaagggccc gtcaacacgt cgtcattgct | 420 |
| accgccagct ggcacccaca catcaccgac cctttttttc cattttcggc tgggccgtta | 480 |
| gtgggatccg cccgctcccg gagattttca cttggatttg cgcgtcccct ttttttcttc | 540 |
| attctctgac tcccctacc ttctcccact tttctgtgta tcaagaggaa aagaaggaga | 600 |
| aaaggagaac tccgaaaaat accgaacaag agggtaacag aatgtgcatt tggatgagcg | 660 |
| ggtaacagat ggaagtacgc tccaaaagaa gggtaatatg ttctgctttt ttttatcatt | 720 |
| atttttctttt acatcctgtg gaactctatg gaaaagtaag gaacttcagc gcgaaataac | 780 |
| gttctgactg ataaaaatta aggaatgagg catataacga acaaatcgca ctccacctgg | 840 |
| acaaaaaaaa aaaagagag agaagtccta tatcatactc taaacataac ataacaatgg | 900 |
| cttttccaaca aggtgtattg tcaaggtgtt ccggtgtctt tagacaccat gtgggacatt | 960 |
| ctcgccatat caataatatt ctttatagac atgccatcgc gtttgcatcc atcgctccac | 1020 |
| gaataccaaa atctagcttc catacttctg caatcagaaa caacgaagca ttcaaggacc | 1080 |
| cgtacgatac tttaggcttg aagaaatctg ctacaggtgc ggaaatcaaa aaagcatact | 1140 |
| acaaactggc aaagaagtac caccccggata tcaacaagga accggatgct gagaagaaat | 1200 |
| tccacgattt acagaacgct tatgaaattc tgtcagacga aacgaagagg cagcagtacg | 1260 |
| atcaatttgg gcccgctgcc ttcggcgcg cggtgccgc tggaggtgcc ggtggtggta | 1320 |
| gtggctctcc ctttggttcc caatttcatg atttctcagg attcaccagt gcaggcggct | 1380 |
| cgccatttgg cggtatcaat tttgaagacc tgtttggtgc tgcatttggt ggtggtggcc | 1440 |
| gcggtagcgg tggcgcaagc aggtcgtcat ctatgttcag acaatatagg ggcgacccaa | 1500 |
| tcgagattgt ccataaagtg tctttcaagg acgcagtgtt tgggtccaag aacgttcagt | 1560 |
| taagattctc tgcgctggac ccttgtagta cctgttcagg gacgggaatg aaaccaaaca | 1620 |
| cgcataaggt cagttgtagc acttgtcacg gaacaggaac cactgttcac attaggggcg | 1680 |

```
gatttcagat gatgtcgact tgtcctactt gcaacggtga aggtaccatg aaacggcctc      1740
aggacaattg taccaagtgc catggtgagg gtgttcaggt caacagggca aagacaatta      1800
cggtggactt gccacatgga ttacaggacg gcgacgtggt caggatccct ggccaaggct      1860 catacccctga catcgctgta gaggcggact tgaaagattc agtcaagtta tcaagaggtg     1920
atattttggt gagaattcgt gtcgacaagg atcccaactt ttcgataaag aacaagtacg      1980
atatttggta cgacaaggag attcctataa ccacagctgc acttggtggt actgtcacta     2040
tccccactgt ggagggacaa aagatcagga taaaggtcgc tccagggact caatacaatc     2100
aagtgatatc cattcctaac atgggtgttc ctaaaacatc aaccattcgc ggtgatatga     2160
aagtccagta caagatcgtt gttaagaaac cgcaatcgct ggcagaaaaa tgcttgtggg     2220
aggcactggc agatgtcacc aacgatgaca tggccaagaa accatgcaa ccgggcacag      2280 ccgcgggtac agccattaat gaagagatac tgaagaaaca aaaacaagaa gaggaaaaac     2340
acgcaaaaaa ggatgacgac aacactttga gagactaga aaatttcatt accaacacat      2400
tcaggaagat caaaggtgac aaaaaaaatt aaacttcatg caatttcttg tagataagga     2460
aaaatagaag cctttacgta aatagataac tatagttaaa taattgtgca taaaagaacc     2520
aacgatttat accttatttt ttttttttt ttttattta tttttttttt ttttgcgtaa       2580
tacaagcgaa ggcattgttt acatgccaaa acccaaaact gagctcgag                 2629

<210> SEQ ID NO 6
<211> LENGTH: 2178
<212> TYPE: DNA
<213> ORGANISM: Saccharomyces cerevisiae

<400> SEQUENCE: 6
gcctctatca ctgcaaagtg tttattagcg ccaaatgaca actctaaaac taagaaagga        60
gtttttaagc accgcctcat aagttgtact ggtgaaagaa tgtctgaagt catatccaaa       120
gtttattctg acacaagaat aacaactttt cttcctgaac attctaatgg tttgagtaac       180
gaatttaggt gctacgcaaa ttttgaatgt agttcatgga aatttgcttc ttgagctttt       240
taagagcttc gataaatttg aaaattaatt gtactacata aaaaatatgt aaacatcaat       300
atatataata taatcacatt tcaaatatat cacgtgttat atttactata taaaaattca       360
ataaataaaa agttagaaga taaaaattat attatacata tttttatttt tattataatt       420 tttgttttg ccttccgaaa agaaaatagt tttttgtatt acggaaatta cagaaaaatg        480
tttaattttg atttcatatt ttttctttct ttgaaagaat attgacgaca aagtattgga       540
taattataat gcaaggaaag gatatttgta gatcttcggt tcaatgaaag ttaatgcggt       600
atgaatattg ctttctccag gacctttttt tttttttaga ggctatttta ttgtcggtgt       660
ttgtggattt tatatttctc ggtccgatag tccctataga tcgttattg ttctctcgag        720 aaatggtatc gtttaaaaat ctcatataag cctgcaagga aaagattatg ctgcagctat       780
aaaatagaat agacaacaat atagattgtc aattttgtcc aattttatt gcaactctac        840 ctggaagggc aaacaaaaat aaatatgtca agatagatt cagttttaat tatcggtggt        900
tctggttttc ttggattgca cttaattcag caattttttg atattaatcc taagccagac       960
atccacattt ttgatgttag agatctccct gaaaacttt caaacagtt tacttttaat       1020 gtagacgaca taaatttca taagggtgat ttaacatcac ctgatgatat ggaaaacgca      1080
attaacgaaa gtaaagcaaa tgttgttgtt cattgtgctt ctccaatgca tggtcaaaat      1140
ccagatattt atgacatagt gaatgttaag ggaacccgta acgtgataga tatgtgcaag      1200
```

```
aaatgtggcg ttaatatact tgtatatact tcctctgctg gtgttatttt taatgggcaa    1260
gatgtgcaca atgcagacga aacctggcca atcccagaag ttcctatgga tgcgtacaat    1320
gagactaaag ctatcgccga agatatggtc ttgaaggcga atgatccaag cagtgatttc    1380
tatactgttg ctcttcgtcc agctggtatt tttggcccag gtgataggca attagtacct    1440
ggtctaagac aggttgcgaa attggggcag tcgaagttcc aaattggtga taataacaat    1500
ctatttgatt ggacttatgc tggaaatgtt gctgacgcgc atgtgttagc tgcacagaaa    1560
cttctcgatc caaaaacaag aactgctgtc tcgggtgaaa cttttttcat taccaatgat    1620
acccccacct attttgggc cttggcccgt actgtgtgga aggcagatgg tcatattgat     1680
aaacatgtta ttgttttgaa aaggccagtt gcaatttgtg caggttatct ttcagaatgg    1740
gtatccaaga tgctgggtaa agagccaggt ttgactccat tcagagtcaa gattgtgtgt    1800
gcataccgtt atcacaacat tgctaaggcc aaaaagttgc taggctacac accaagagtt    1860
ggtattgaag aaggaattaa caaaacgttg gcctggatgg acgaaggttt gtaatggcaa    1920
tcgttaggag ctttttgatc cgattatcga aagatagtat gttgaaatag catatctgat    1980
acgcaccgta tatatttatt ctgtctttat agatgaataa taagaattga aacacctaaa    2040
acatcttgat gactaggtta gtatatatat gtatacactc atttaatgac tacactatga    2100
agcgtcgggg taatgcatgt aaataaatag aaataaatca ttgaaacaac gaaattctca    2160
tgtatgcctg ctaaggat                                                  2178
```